(12) United States Patent
Voytik-Harbin et al.

(10) Patent No.: US 9,867,905 B2
(45) Date of Patent: Jan. 16, 2018

(54) COLLAGEN-BASED MATRICES WITH STEM CELLS

(75) Inventors: Sherry L. Voytik-Harbin, Zionsville, IN (US); Seth Kreger, New Richmond, IN (US); Mervin C. Yoder, Indianapolis, IN (US); Paul Critser, Indianapolis, IN (US)

(73) Assignees: PURDUE RESEARCH FOUNDATION, West Lafayette, IN (US); INDIANA UNIVERSITY RESEARCH AND TECHNOLOGY CORPORATION, Indianapolis, IN (US)

( * ) Notice: Subject to any disclaimer, the term of this patent is extended or adjusted under 35 U.S.C. 154(b) by 533 days.

(21) Appl. No.: 12/332,084

(22) Filed: Dec. 10, 2008

(65) Prior Publication Data

US 2009/0280180 A1 Nov. 12, 2009

Related U.S. Application Data

(60) Provisional application No. 61/012,713, filed on Dec. 10, 2007, provisional application No. 61/062,015, filed on Jan. 23, 2008.

(51) Int. Cl.
*A61L 27/50* (2006.01)
*A61L 27/24* (2006.01)
*A61L 27/38* (2006.01)

(52) U.S. Cl.
CPC ............ *A61L 27/507* (2013.01); *A61L 27/24* (2013.01); *A61L 27/3808* (2013.01); *A61L 27/3834* (2013.01)

(58) Field of Classification Search
CPC .. A61L 27/24; A61L 27/3817; A61L 27/3834; C07K 14/78; C12N 5/0656; C12N 5/0663; C12N 5/0667
See application file for complete search history.

(56) References Cited

U.S. PATENT DOCUMENTS

| | | | |
|---|---|---|---|
| 3,949,073 A | 4/1976 | Daniels et al. | |
| 4,233,360 A | 11/1980 | Luck et al. | |
| 4,544,516 A | 10/1985 | Hughes et al. | |
| 4,582,640 A | 4/1986 | Smestad et al. | |
| 4,789,663 A | 12/1988 | Wallace et al. | |
| 4,902,508 A | 2/1990 | Badylak et al. | |
| 4,956,178 A | 9/1990 | Badylak et al. | |
| 5,163,955 A | 11/1992 | Love et al. | |
| 5,204,382 A | 4/1993 | Wallace et al. | |
| 5,275,826 A | 1/1994 | Badylak et al. | |
| 5,281,422 A | 1/1994 | Badylak et al. | |
| 5,420,248 A | 5/1995 | Devictor et al. | |
| 5,554,389 A | 9/1996 | Badylak et al. | |
| 5,885,619 A | 3/1999 | Patel et al. | |
| 5,948,429 A | 9/1999 | Bell et al. | |
| 5,955,110 A | 9/1999 | Patel et al. | |
| 6,099,567 A | 8/2000 | Badylak et al. | |
| 6,206,931 B1 | 3/2001 | Cook et al. | |
| 6,264,992 B1 | 7/2001 | Voytik-Harbin et al. | |
| 6,375,989 B1 | 4/2002 | Badylak et al. | |
| 6,384,196 B1 | 5/2002 | Weis et al. | |
| 6,444,229 B2 | 9/2002 | Voytik-Harbin et al. | |
| 6,497,875 B1 | 12/2002 | Sorrell et al. | |
| 6,576,265 B1 | 6/2003 | Spievack | |
| 6,592,623 B1 | 7/2003 | Bowlin et al. | |
| 6,592,794 B1 | 7/2003 | Bachrach | |
| 6,666,892 B2 | 12/2003 | Hiles et al. | |
| 6,793,939 B2 | 9/2004 | Badylak | |
| 8,084,055 B2 * | 12/2011 | Voytik-Harbin et al. | 424/443 |
| 8,512,756 B2 * | 8/2013 | Voytik-Harbin et al. | 424/491 |
| 2002/0076816 A1 | 6/2002 | Dai et al. | |
| 2002/0170120 A1 | 11/2002 | Eckmayer et al. | |
| 2002/0172705 A1 | 11/2002 | Murphy et al. | |
| 2004/0037813 A1 * | 2/2004 | Simpson et al. | 424/93.7 |
| 2004/0078076 A1 | 2/2004 | Badylak et al. | |
| 2005/0014181 A1 | 1/2005 | Galis et al. | |
| 2005/0019419 A1 | 1/2005 | Badylak et al. | |
| 2005/0153442 A1 | 7/2005 | Katz et al. | |
| 2005/0226856 A1 * | 10/2005 | Ahlfors | 424/93.7 |
| 2005/0266556 A1 | 12/2005 | Yoder et al. | |
| 2006/0147501 A1 * | 7/2006 | Hillas et al. | 424/443 |
| 2006/0235511 A1 | 10/2006 | Osborne | |
| 2007/0026518 A1 * | 2/2007 | Healy et al. | 435/325 |
| 2007/0077652 A1 | 4/2007 | Peled et al. | |
| 2007/0269476 A1 | 11/2007 | Voytik-Harbin et al. | |
| 2008/0025956 A1 * | 1/2008 | Yoder et al. | 424/93.7 |
| 2008/0199441 A1 | 8/2008 | Peled | |
| 2008/0268052 A1 | 10/2008 | Voytik-Harbin et al. | |

(Continued)

FOREIGN PATENT DOCUMENTS

DE 201 15 753 U1 1/2002
EP 0443094 8/1991

(Continued)

OTHER PUBLICATIONS

Korff et al Journal of Cell Science, 1999, 112, 3249-3258.*
Ingram et al Blood, 2005, Blood, 2004, 104 (9), 2752-2760.*
Sieminski et al Experimental Cell Research 297 (2004) 574- 584.*
Pizzo et al Journal of Applied Physiology, 2005, 98: 1909-1921.*
Kreger et al , Biopolymers, 2010, 93 (8), 690-707.*
Wang et al (Sheng Li Xue Bao. Apr. 25, 2005;57(2):259-69, abstract only.*
Williams et al J. Biol. Chem. 1978, 253:6578-6585.*
Roeder et al J Biomech Eng 124(2), 214-222 (Mar. 29, 2002.*
Akhavani et al Journal of Plastic, Reconstructive & Aesthetic Surgery (2008) 61, 1425e1437.*
Asahara et al Circ Res. 1999; 85:221-228.*
Bailey et al Biopolymer, 2010, vol. 95, 2 77-93.*

(Continued)

*Primary Examiner* — Anoop K Singh
(74) *Attorney, Agent, or Firm* — Valauskas Corder LLC

(57) ABSTRACT

Collagen based-matrices and methods of their use are described. More particularly, collagen-based matrices for differentiating stem cells and progenitor cells, and for producing and isolating blood vessels and vascularized graft constructs are described.

3 Claims, 25 Drawing Sheets

(56) References Cited

U.S. PATENT DOCUMENTS

| | | | |
|---|---|---|---|
| 2009/0011021 | A1 | 1/2009 | Voytik-Harbin et al. |
| 2009/0069893 | A1 | 3/2009 | Paukshto et al. |
| 2009/0175922 | A1 | 7/2009 | Voytik-Harbin et al. |

FOREIGN PATENT DOCUMENTS

| | | | |
|---|---|---|---|
| EP | 1264878 | | 12/2002 |
| EP | 1 270 672 A1 | | 1/2003 |
| EP | 1 674 116 A2 | | 6/2006 |
| GB | 2366736 | | 3/2002 |
| JP | 07 074239 B | | 8/1995 |
| WO | 1994/03119 | | 2/1994 |
| WO | 2001/023529 | | 4/2001 |
| WO | 2001/045765 | | 6/2001 |
| WO | 2002/102237 | | 12/2002 |
| WO | 2003/068287 | | 8/2003 |
| WO | 2003/071991 | | 9/2003 |
| WO | 2003/087337 | | 10/2003 |
| WO | 2003/097694 | | 11/2003 |
| WO | WO/2003/097694 | * | 11/2003 |
| WO | 2004/060426 | | 7/2004 |
| WO | 2004/078120 | | 9/2004 |
| WO | 2006/003442 | | 1/2006 |
| WO | 2006/124946 | | 11/2006 |
| WO | 2006/125025 | | 11/2006 |
| WO | WO/2006/124946 | * | 11/2006 |
| WO | 2007/028079 | | 3/2007 |
| WO | 2007/136634 | | 11/2007 |
| WO | 2008/036393 | | 3/2008 |
| WO | 2010/123928 | | 10/2010 |
| WO | 2011/009054 | | 1/2011 |

OTHER PUBLICATIONS

"Basement Membrane" accessed online at http://en.wikipedia.org/wiki/Basement_membrane#Composition on Jun. 11, 2010.

"Extracellular Matrix" accessed at http://en.wikipedia.org/wiki/Extracellular_matrix on Jun. 11, 2010.

Bell, Brett J. et al., "Cell Density and Extracellular Matrix (ECM) Microstructure Control Mechanical Behavior of Engineered Tissue Constructs", *2005 Summer Bioengineering conference*, (Jun. 22-26, 2005).

Bjornsson, S., "Simultaneous Preparation and Quantitation of Proteoglycans by Precipitation with Alcian Blue", Analytical Biochemistry, vol. 210, 1993, pp. 282-291.

Brightman et al., "Time-Lapse Confocal Reflection Microscopy of Collagen Fibrillogenesis and Extracellular Matrix Assembly In Vitro", *Biopolymers*, vol. 54, 222-234, (2000).

Callister, W. D, Jr., Materials Science and Engineering: an Introduction, $3^{rd}$ edition, New York, NY, John Wiley & Sons, Inc., 1994.

Chandrakasan et al.,"Preparation of Intact Monomeric Collagen from Rat Tail Tendon and Skin and the Structure of the Nonhelical Ends in Solution," J. Biol. Chem., 1976, 251:6062-67.

Ciovacco et al., "The role of gap junctions in megakaryocyte-mediated osteoblast proliferation and differentiation," Bone, 2009, 44(1):80-86.

Comper, W. D., and A. Veis, "Characterization of Nuclei in in Vitro Collagen Fibril Formation", Biopolymers, vol. 16, 1977, pp. 2133-2142.

Compston, "Bone marrow and bone: a functional unit," Journal of Endocrinology, 173: 387-394, 2002.

Davis, et al., "Injectable Self-Assembling Peptide Nanofibers Create Intramyocardial Microenvironments for Endothelial Cells", *Circulation*, 111, 442-50, (Feb. 1, 2005).

Fulzele, S. V., P. M. Satturwar, A. K. Dorle, "Study of the Biodegradation and in Vivo Biocompatibility of Novel Biomaterials", European Journal of Pharmaceutical Sciences, vol. 20, 2003, pp. 53-61.

Gallop, P. M., and S. Seifter, "Preparation and Properties of Soluble Collagens", Soluble Collagens, 1963, pp. 635-641.

Gelman et al., "Collagen Fibril Formation in Vitro," J. Biol. Chem., 1979, 254(22): 11741-11745.

Gelman et al., "Collagen Fibril Formation," J. Biol. Chem., 1979, 254(1):180-186.

Griffey, S., N. D. Schwade, C. G. Wright, "Particulate Dermal Matrix as an Injectable Soft Tissue Replacement Material", J. Biomed. Mater. Res. vol. 58, 2001, pp. 10-15.

Hou, et al., "Radiolabeled Cell Distribution After Intramyocardial, Intracoronary, and Interstitial Retrograde Coronary Venous Delivery", *Circulation*, 112, 150-6, (Aug. 30, 2005).

Hunt, T. K., P. Twomey, B. Zederfeldt, and J. E. Dunphy, "Respiratory Gas Tensions and PH in Healing Wounds", American Journal of Surgery, vol. 114, 1967, pp. 302-307.

Kacena et al., "Evaluation of Two Different Methylmethacrylate Processing, Infiltration, and Embedding Techniques on the Histological, Histochemical, and Immunohistochemical Analusis of Murine Bone Spoecimens" J. of Histotechnology, 2004, 27:119-130.

Knott et al., "Collagen Cross-Links in Mineralizing Tissues: A Review of Their Chemistry, Function, and Clinical Relevance," 1998, 22(3):181-187.

Kondo et al., " Biology of Hematopoietic Stem Cells and Progenitors: Implications for Clinical Application," Annu. Rev. Immunol., 2003, 21:759-806.

Kreger et al., "Hyaluronan concentration within a 3D collagen matrix modulates matrix viscoelasticity, but not fibroblast response," Matrix Biol., 2009, 28(6):336-46.

Kreger, "Design of 3D Collagen Matrices for Cell Delivery and Guidance in Tissue Engineering," Thesis Submitted to the Faculty of Purdue University in Partial Fulfillment of the Requirements for the Degree of Doctor of Philosophy, May 2009, Purdue University.

Lin et al., "Comparison of Physical-Chemistry Properties of Type I Collagen from Different Species," *Food Chemistry*, 99(2): 244-251 (2005).

Malvern, *Introduction to the Mechanics of a Continuous Medium*. Upper Saddle River, NJ: Prentice-Hall, 1969.

Marotta, M., G. Martino, "Sensitive Spectrophotometric Method for the Quantitative Estimation of Collagen", Analytical Biochemistry, vol. 150, 1985, pp. 86-90.

Miller et al., "Preparation and Characterization of the Different Types of Collagen," *Methods in Enzymology*, 82: 33-64 (1982).

Miller, E. J., E. H. Epstein, Jr., and K. A. Piez, "Identification of Three Genetically Distinct Collagens by Cyanogen Bromide Cleavage of Insoluble Human Skin and Cartilage Collagen", Biochemical and Biophysical Research Communications, vol. 42, No. 6, 1971, pp. 1024-1029.

Na, "Monomer and Oligomer of Type I Collagen: Molecular Properties and Fibril Assembly," 1989, 28(18):7161-67.

Narmoneva et al., "Endothelial Cells Promote Cardiac Myocyte Survival and Spatial Reorganization", *Circulation*, 110, 962-968, (Aug. 24, 2004).

Nguyen et al., "Comparison of the Amino Acid Composition of Two Commercial Porcine Skins (Rind)," *Journal of Agricultural and Food Chemistry*, 34(3): 565-572 (1986).

Nielsen, T. B. and J. A. Reynolds, "Measurements of Molecular Weights by Gel Electrophoresis", Methods in Enzymology, vol. 48, Hirs and Temasheff, Eds., Academic Press, New York, 1978, pp. 3-10.

Orschell-Traycoff et al., "Homing and engraftment of Sca-1+lin-cells fractionated on the basis of adhesions molecule expression and position in cell cycle," Blood, 2000, 96:1380-1387.

Osborne, et al., "Investigation into the tensile properties of collagen/chondroitin-6-sulphate gels: the effect of crosslinking agents and diamines", *Medical & Biological Engineering & Computing*, vol. 36, 129-134, (1998).

Ozerdem, et al., "Physical Response of Collagen Gels to Tensile Strain", *Journal of Biomechanical Engineering*, vol. 117, 397-401, (Nov. 1995).

Pizzo et al., "Cell-Extracellular Matrix (ECM) Micro-Mechanical Behavior Depends on ECM Microstructure and Cell Type", *2005 Summer Bioengineering Conference*, (Jun. 22-26, 2005).

(56) References Cited

OTHER PUBLICATIONS

Pizzo et al., "Long-term Production of Choline Acetylatransferase in the CNS After Transplantation of Fibroblasts Modified with a Regulatable Vector", *Mol Brain Res*, 126, 1-13 (2004).

Rehman, et al., "Secretion of Angiogenic and Antiapoptotic Factors by Human Adipose Stromal Cells", *Circulation*, 109: 1292-8, (Mar. 16, 2004).

Reinlib, et al., "Cell Transplantation as Future Therapy for Cardiovascular Disease?", *Circulation*, 101: e182-e187, (2000).

Roeder B. A., K. Kokini, J. E. Sturgis, J. P. Robinson, S. L. Voytik-Harbin, "Tensile Mechanical Properties of Three-Dimensional Type 1 Collagen Extracellular Matrices with Varied Microstructure", J. Biomech. Eng., vol. 124, 2002, pp. 214-222.

Roeder et al., "Local, Three-Dimensional Strain Measurements Within Largely Deformed Extracellular Matrix Constructs", *J Biomech Eng*, 126, 699-708, (2004).

Scadden, "The stem cell niche as an entity of action," Nature, 441: 1075-1079, 2006.

Schechner et al., "In vivo formation of complex microvessels lined by human endothelial cells in an immunodeficient mouse," *PNAS*, Aug. 1, 2000, vol. 97, No. 16, 9191-9196.

Schilling, J. A., W. Joel, H. M. Shurley, "Wound Healing: A Comparative Study of the Histochemical Changes in Granulation Tissue Contained in Stainless Steel Wire Mesh and Polyvinyl Sponge Cylinders", Surgery, vol. 46, No. 4, Oct. 1959, pp. 702-710.

Shiozawa et al., "The bone marrow niche: habitat to hematopoietic and mesenchymal stem cells, and unwitting host to molecular parasites," Leukemia, 22(5): 941-950, 2008.

Spradling et al., "Stem Cells Find Their Niche," Nature, 414,:98-104 2001.

Strang, et al., *Linear Algebra and Its Applications*. 3rd edition. San Diego, CA: Academic Press, 1988.

Sykes, B., B. Puddle, M. Francis, and R. Smith, "The Estimation of Two Collagens from Human Dermis by Interrupted Gel Electrophoresis", Biochemical and Biophysical Research Communications, vol. 72, No. 4, 1976, pp. 1472-1480.

Veis, Arthur, et al., "Fundamentals of Interstitial; Collagen Self-Assembly", 1994, Extracellular Matrix Assembly and Structure, Academic Press, pp. 15-45.

Voytik-Harbin et al., "Application and Evaluation of the Alamarblue Assay for Cell Growth and Survival of Fibroblasts", *In Vitro Cell Dev Biol Anim*, 34, 239-246, (1998).

Voytik-Harbin et al., "Simultaneous Mechanical Loading and Confocal Reflection Microscopy for Three-Dimensional Microbiomechanical Analysis of Biomaterials and Tissue Constructs", *Microsc Microanal*, 9, 74-85, (2003).

Voytik-Harbin et al., Small Intestinal Submucosa: A Tissue-Derived Extracellular Matrix That Promotes Tissue-Specific Growth and Differentiation of Cells in Vitro, *Tissue Engineering*, 4, 2, 157-174, (1998).

Voytik-Harbin et al., "Three-Dimensional Imaging of Extracellular Matrix and Extracellular Matrix-Cell Interactions", *Methods in Cell Biology*, 63, 583-597, (2001).

Wess, Collagen fibrillar structure and hierarchies in P. Fratzl (ed.), Collagen: Structure and Mechanics, Springer Science + Business Media, LLC, New York, 2008, 53-60.

Yoder et al., "Redefining endothelial progenitor cells via clonal analysis and hematopoietic stem/progenitor cell principals," *BLOOD*, 2007, 109:1801-1809.

International Search Report and Written Opinion for PCT/US2008/086232 completed Jan. 16, 2009, 12 pages.

Bailey JL et al., "Collagen Oligomers Modulate Physical and Biological Properties of Three-Dimensional Self-Assembled Matrices," Biopolymers, 2010; 95(2): 77-93.

Na et al., "In Vitro Collagen Fibril Assembly in Glycerol Solution: Evidence for a Helical Cooperative Mechanism Involving Microfibrils," Biochemistry, 1986; 25: 958-966.

Na et al., "Mechanism of in Vitro Collagen Fibril Assembly," Journal of Biological Chemistry, 1986; 261(26): 12290-12299.

Voytik-Harbin et al., "Identification of Extractable Growth Factors from Small Intestine Submucosa," J Cell. Biochemistry, 1997; 67: 478-491.

Condell RA et al., "Analysis of Native Collagen Monomers and Oligomers by Size-Exclusion High-Performance Liquid Chromatography and its Application," Analytical Biochemistry, 1993; 212: 436-445.

* cited by examiner

A

B

COLLAGEN-BASED MATRICES WITH STEM CELLS

CROSS REFERENCE TO RELATED APPLICATIONS

This application claims the benefit under 35 U.S.C. §119(e) of U.S. Provisional Application Ser. No. 61/012,713 filed on Dec. 10, 2007, incorporated herein by reference in its entirety. This application also claims the benefit under 35 U.S.C. §119(e) of U.S. Provisional Application Ser. No. 61/062,015, filed on Jan. 23, 2008, incorporated herein by reference in its entirety.

STATEMENT CONCERNING FEDERALLY SPONSORED RESEARCH

This invention was made with government support under R01 EB000165 awarded by the National Institutes of Health. The government has certain rights in the invention.

FIELD OF THE INVENTION

This invention relates to collagen based-matrices and methods of their use. More particularly, the invention relates to collagen-based matrices for culturing and differentiating stem cells, and for producing vessels and tissue grafts with vessels.

BACKGROUND AND SUMMARY

Vascular network formation is a limiting obstacle for tissue engineering strategies targeting repair and regeneration of damaged or diseased tissue. Development of functional vascular networks is important for the treatment of various diseases, such as, diabetic ulcers, limb ischemia, cerebral ischemia, peripheral vascular disease, and cardiovascular disease. Therapeutic use of stem and progenitor cells for the treatment of diseases or dysfunctional tissues has been limited by the ability to control their survival, proliferation, and differentiation. Recently, three-dimensional (3D) extracellular matrices (ECMs) have been identified as an important component of stem cell technology to assist in guiding cell behavior. However, tissue engineering approaches with engineered collagen matrices to generate functional vascular networks, needed for the treatment of peripheral and cardiovascular disease, have not been previously developed.

Applicants have engineered collagen-based matrices with the potential to direct vessel formation. Mechanical properties including fiber diameter, fibril density, fibril length, and matrix stiffness can be modulated by controlling polymerization parameters including collagen concentration, temperature, pH, ionic strength, and polymerization time. Applicants describe engineered collagen-based matrices that modulate in vitro and in vivo vessel formation to improve the efficiency of cellular-based therapies to regenerate or repair blood vessels. Systemic variation of polymerization conditions such as pH, ionic strength, and molecular composition provides a means to control polymerization kinetics, fibril microstructure, and mechanical properties of 3D collagen matrices. These microstructural-mechanical properties, in turn, provide instructional information to stem cells, and have been used by Applicants as design parameters to influence cell behavior.

In one illustrative embodiment, a composition for supporting stem cells is provided, the composition comprising an engineered, purified collagen-based matrix comprising collagen fibrils, and a population of stem cells, wherein the fibril volume fraction of the matrix is about 1% to about 60%, and wherein the storage modulus of the matrix is about 10 Pa to about 700 Pa.

In the above described embodiment, the stem cells can be mesenchymal stem cells, the fibril volume fraction of the matrix can be about 20%, the storage modulus of the matrix can be about 40 Pa to about 50 Pa, the stem cells can be differentiated into adipocytes, the fibril volume fraction of the matrix can be about 50% to about 60%, the storage modulus of the matrix can be about 650 Pa to about 700 Pa, the stem cells can be differentiated into osteoblasts, or the seeding density of the stem cells can be about $0.3 \times 10^4$ cells/ml to about $60 \times 10^4$ cells/ml.

In another illustrative embodiment, a composition for supporting stem cells is provided, the composition comprising an engineered, purified collagen-based matrix comprising collagen fibrils, and a population of stem cells, wherein the fibril volume fraction of the matrix is about 1% to about 60%, and wherein the loss modulus of the matrix is about 1 Pa to about 75 Pa.

In the above described embodiment, the stem cells can be mesenchymal stem cells, the fibril volume fraction of the matrix can be about 20%, the storage modulus of the matrix can be about 40 Pa to about 50 Pa, the stem cells can be differentiated into adipocytes, the fibril volume fraction of the matrix can be about 50% to about 60%, the storage modulus of the matrix can be about 650 Pa to about 700 Pa, the stem cells can be differentiated into osteoblasts, or the seeding density of the stem cells can be about $0.3 \times 10^4$ cells/ml to about $60 \times 10^4$ cells/ml.

In a further illustrative embodiment, a composition for supporting stem cells is provided, the composition comprising an engineered, purified collagen-based matrix comprising collagen fibrils, and a population of stem cells, wherein the fibril volume fraction of the matrix is about 1% to about 60%, and wherein the compressive modulus of the matrix is about 2500 Pa to about 18,000 Pa.

In the above described embodiment, the stem cells can be mesenchymal stem cells, the fibril volume fraction of the matrix can be about 20%, the storage modulus of the matrix can be about 40 Pa to about 50 Pa, the stem cells can be differentiated into adipocytes, the fibril volume fraction of the matrix can be about 50% to about 60%, the storage modulus of the matrix can be about 650 Pa to about 700 Pa, the stem cells can be differentiated into osteoblasts, or the seeding density of the stem cells can be about $0.3 \times 10^4$ cells/ml to about $60 \times 10^4$ cells/ml.

In yet another illustrative embodiment, a tissue graft composition is provided, the composition comprising an engineered, purified collagen-based matrix comprising collagen fibrils, and a population of stem cells, wherein the fibril volume fraction of the matrix is about 1% to about 60%, and wherein the storage modulus of said matrix is about 10 Pa to about 700 Pa.

In the above described embodiment, the stem cells can be mesenchymal stem cells, the fibril volume fraction of the matrix can be about 20%, the storage modulus of the matrix can be about 40 Pa to about 50 Pa, the stem cells can be differentiated into adipocytes, the fibril volume fraction of the matrix can be about 50% to about 60%, the storage modulus of the matrix can be about 650 Pa to about 700 Pa, the stem cells can be differentiated into osteoblasts, or the seeding density of the stem cells can be about $0.3 \times 10^4$ cells/ml to about $60 \times 10^4$ cells/ml.

In a further illustrative embodiment, a tissue graft composition is provided, the composition comprising an engineered, purified collagen-based matrix comprising collagen fibrils, and a population of stem cells, wherein the fibril volume fraction of the matrix is about 1% to about 60%, and wherein the loss modulus of the matrix is about 1 Pa to about 75 Pa.

In the above described embodiment, the stem cells can be mesenchymal stem cells, the fibril volume fraction of the matrix can be about 20%, the storage modulus of the matrix can be about 40 Pa to about 50 Pa, the stem cells can be differentiated into adipocytes, the fibril volume fraction of the matrix can be about 50% to about 60%, the storage modulus of the matrix can be about 650 Pa to about 700 Pa, the stem cells can be differentiated into osteoblasts, or the seeding density of the stem cells can be about $0.3 \times 10^4$ cells/ml to about $60 \times 10^4$ cells/ml.

In a further illustrative embodiment, a tissue graft composition is provided, the composition comprising an engineered, purified collagen-based matrix comprising collagen fibrils, and a population of stem cells, wherein the fibril volume fraction of the matrix is about 1% to about 60%, and wherein the compressive modulus of the matrix is about 2500 Pa to about 18,000 Pa.

In the above described embodiment, the stem cells can be mesenchymal stem cells, the fibril volume fraction of the matrix can be about 20%, the storage modulus of the matrix can be about 40 Pa to about 50 Pa, the stem cells can be differentiated into adipocytes, the fibril volume fraction of the matrix can be about 50% to about 60%, the storage modulus of the matrix can be about 650 Pa to about 700 Pa, the stem cells can be differentiated into osteoblasts, or the seeding density of the stem cells can be about $0.3 \times 10^4$ cells/ml to about $60 \times 10^4$ cells/ml.

In another illustrative embodiment, a method of preparing a tissue graft composition is provided, the method comprising the steps of engineering a purified collagen-based matrix comprising collagen fibrils, and contacting the matrix with a population of stem cells, wherein the fibril volume fraction of the matrix is about 1% to about 60%, and wherein the storage modulus of the matrix is about 10 Pa to about 700 Pa.

In the above described embodiment, the stem cells can be mesenchymal stem cells, the fibril volume fraction of the matrix can be about 20%, the storage modulus of the matrix can be about 40 Pa to about 50 Pa, the stem cells can be differentiated into adipocytes, the fibril volume fraction of the matrix can be about 50% to about 60%, the storage modulus of the matrix can be about 650 Pa to about 700 Pa, the stem cells can be differentiated into osteoblasts, or the seeding density of the stem cells can be about $0.3 \times 10^4$ cells/ml to about $60 \times 10^4$ cells/ml.

In another illustrative embodiment, a method of preparing a tissue graft composition is provided, the method comprising the steps of engineering a purified collagen-based matrix comprising collagen fibrils, and contacting the matrix with a population of stem cells, wherein the fibril volume fraction of the matrix is about 1% to about 60%, and wherein the loss modulus of the matrix is about 1 Pa to about 75 Pa.

In the above described embodiment, the stem cells can be mesenchymal stem cells, the fibril volume fraction of the matrix can be about 20%, the storage modulus of the matrix can be about 40 Pa to about 50 Pa, the stem cells can be differentiated into adipocytes, the fibril volume fraction of the matrix can be about 50% to about 60%, the storage modulus of the matrix can be about 650 Pa to about 700 Pa, the stem cells can be differentiated into osteoblasts, or the seeding density of the stem cells can be about $0.3 \times 10^4$ cells/ml to about $60 \times 10^4$ cells/ml.

In another illustrative embodiment, a method of preparing a tissue graft composition is provided, the method comprising the steps of engineering a purified collagen-based matrix comprising collagen fibrils, and contacting the matrix with a population of stem cells, wherein the fibril volume fraction of the matrix is about 1% to about 60%, and wherein the compressive modulus of the matrix is about 2500 Pa to about 18,000 Pa.

In the above described embodiment, the stem cells can be mesenchymal stem cells, the fibril volume fraction of the matrix can be about 20%, the storage modulus of the matrix can be about 40 Pa to about 50 Pa, the stem cells can be differentiated into adipocytes, the fibril volume fraction of the matrix can be about 50% to about 60%, the storage modulus of the matrix can be about 650 Pa to about 700 Pa, the stem cells can be differentiated into osteoblasts, or the seeding density of the stem cells can be about $0.3 \times 10^4$ cells/ml to about $60 \times 10^4$ cells/ml.

In another illustrative embodiment, a tissue graft composition is provided, the composition comprising an engineered, purified collagen-based matrix comprising collagen fibrils, and one or more vessels.

In the above described embodiment, the fibril volume fraction of the matrix can be about 1% to about 60% and the storage modulus of the matrix can be about 10 Pa to about 700 Pa, the fibril volume fraction of the matrix can be about 1% to about 60% and the loss modulus of the matrix can be about 1 Pa to about 75 Pa, the fibril volume fraction of the matrix can be about 1% to about 60% and the compressive modulus of the matrix can be about 2500 Pa to about 18,000 Pa, or the composition can further comprises endothelial progenitor cells.

In another illustrative embodiment, a method of preparing a tissue graft composition is provided, the method comprising the steps of engineering a purified collagen-based matrix comprising collagen fibrils, and contacting the matrix with endothelial progenitor cells wherein one or more vessels are formed within the matrix.

In the above described embodiment, the fibril volume fraction of the matrix can be about 1% to about 60% and the storage modulus of the matrix can be about 10 Pa to about 700 Pa, the fibril volume fraction of the matrix can be about 1% to about 60% and the loss modulus of the matrix can be about 1 Pa to about 75 Pa, or the fibril volume fraction of the matrix can be about 1% to about 60% and the compressive modulus of the matrix can be about 2500 Pa to about 18,000 Pa.

In another illustrative embodiment, a method of promoting vessel formation within a tissue graft composition is provided, the method comprising the steps of engineering a purified collagen-based matrix comprising collagen fibrils, and contacting the matrix with endothelial progenitor cells wherein one or more vessels are formed within the matrix.

In the above described embodiment, the fibril volume fraction of the matrix can be about 1% to about 60% and the storage modulus of the matrix can be about 10 Pa to about 700 Pa, the fibril volume fraction of the matrix can be about 1% to about 60% and the loss modulus of the matrix can be about 1 Pa to about 75 Pa, the fibril volume fraction of the matrix can be about 1% to about 60% and the compressive modulus of the matrix can be about 2500 Pa to about 18,000 Pa, or the vessels can be formed from endothelial progenitor cells.

In another illustrative embodiment, a method of vascularizing a tissue graft composition prior to implantation is provided, the method comprising the steps of engineering a purified collagen-based matrix comprising collagen fibrils, and contacting the matrix with endothelial progenitor cells wherein one or more vessels are formed within the matrix.

In the above described embodiment, the fibril volume fraction of the matrix can be about 1% to about 60% and the storage modulus of the matrix can be about 10 Pa to about 700 Pa, the fibril volume fraction of the matrix can be about 1% to about 60% and the loss modulus of the matrix can be about 1 Pa to about 75 Pa, the fibril volume fraction of the matrix can be about 1% to about 60% and the compressive modulus of the matrix can be about 2500 Pa to about 18,000 Pa, or the vessels can be formed from endothelial progenitor cells.

In another illustrative embodiment, a method of producing a population of stem cells is provided, the method comprising the steps of engineering a purified collagen-based matrix comprising collagen fibrils, and contacting the matrix with endothelial progenitor cells wherein the population of cells is produced.

In the above described embodiment, the method can further comprise the step of isolating the stem cells from the matrix, the stem cells can be isolated from the matrix using a collagenase solution, the fibril volume fraction of the matrix can be about 1% to about 60% and the storage modulus of the matrix can be about 10 Pa to about 700 Pa, the fibril volume fraction of the matrix can be about 1% to about 60% and the loss modulus of the matrix can be about 1 Pa to about 75 Pa, or the fibril volume fraction of the matrix can be about 1% to about 60% and the compressive modulus of the matrix can be about 2500 Pa to about 18,000 Pa.

In a further illustrative embodiment, a method of enhancing CD34 expression on stem cells is provided, the method comprising the steps of engineering a purified collagen-based matrix comprising collagen fibrils, and contacting the matrix with endothelial progenitor cells wherein the cells exhibit enhanced CD34 expression.

In the above described embodiment, the method can further comprise the step of isolating the stem cells from the matrix, the stem cells can be isolated from the matrix using a collagenase solution, the fibril volume fraction of the matrix can be about 1% to about 60% and the storage modulus of the matrix can be about 10 Pa to about 700 Pa, the fibril volume fraction of the matrix can be about 1% to about 60% and the loss modulus of the matrix can be about 1 Pa to about 75 Pa, or the fibril volume fraction of the matrix can be about 1% to about 60% and the compressive modulus of the matrix can be about 2500 Pa to about 18,000 Pa.

In a further illustrative embodiment, a method of producing blood vessels de novo is provided, the method comprising the steps of engineering a purified collagen-based matrix comprising collagen fibrils, contacting the matrix with endothelial progenitor cells wherein the vessels are formed, and isolating the vessels from the matrix.

In the above described embodiment, the vessels can be isolated from the matrix using a collagenase solution, the fibril volume fraction of the matrix can be about 1% to about 60% and the storage modulus of the matrix can be about 10 Pa to about 700 Pa, the fibril volume fraction of the matrix can be about 1% to about 60% and the loss modulus of the matrix can be about 1 Pa to about 75 Pa, or the fibril volume fraction of the matrix can be about 1% to about 60% and the compressive modulus of the matrix can be about 2500 Pa to about 18,000 Pa.

In a further illustrative embodiment, a method of treating a tissue of a patient wherein the tissue is in need of vascularization is provided, the method comprising the steps of engineering a purified collagen-based matrix comprising collagen fibrils, contacting the matrix with endothelial progenitor cells wherein vessels are formed de novo, isolating the vessels from the matrix, and implanting the vessels into the tissue of the patient.

In the above described embodiment, the vessels can be isolated from the matrix using a collagenase solution, the fibril volume fraction of the matrix can be about 1% to about 60% and the storage modulus of the matrix can be about 10 Pa to about 700 Pa, the fibril volume fraction of the matrix can be about 1% to about 60% and the loss modulus of the matrix can be about 1 Pa to about 75 Pa, or the fibril volume fraction of the matrix can be about 1% to about 60% and the compressive modulus of the matrix can be about 2500 Pa to about 18,000 Pa.

In another embodiment, a method of forming vessels in vivo is provided. The method comprises the step of implanting an engineered, purified collagen-based matrix comprising collagen fibrils and endothelial progenitor cells into a patient wherein vessel formation at the implantation site is enhanced in vivo.

In the above described embodiment, the fibril volume fraction of the matrix can be about 1% to about 60% and the storage modulus of the matrix can be about 10 Pa to about 700 Pa, the fibril volume fraction of the matrix can be about 1% to about 60% and the loss modulus of the matrix can be about 1 Pa to about 75 Pa, or the fibril volume fraction of the matrix can be about 1% to about 60% and the compressive modulus of the matrix can be about 2500 Pa to about 18,000 Pa.

BRIEF DESCRIPTION OF THE DRAWINGS

Table 1 shows a summary of the specific collagen polymerization reaction conditions used to systematically vary fundamental fibril microstructure and viscoelastic properties of engineered 3D matrices.

Table 2 shows a summary of the relative expression of cell surface markers CD34, CD133, and PECAM in CBFs seeded within 3D extracellular matrices (ECMs) compared to plastic.

DESCRIPTION OF THE ILLUSTRATIVE EMBODIMENTS

Figure 1:
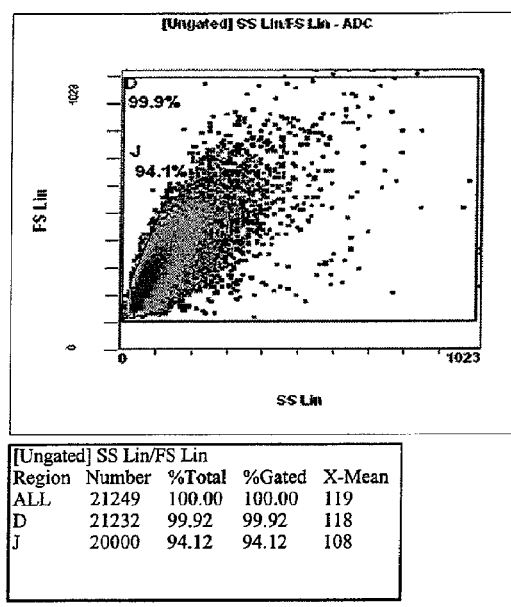
FIG. 1 shows flow cytometry data for quantification of CD34 in CBF cells.
Figure 1:
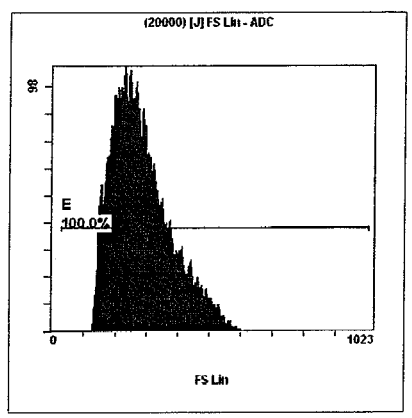
Figure 1:
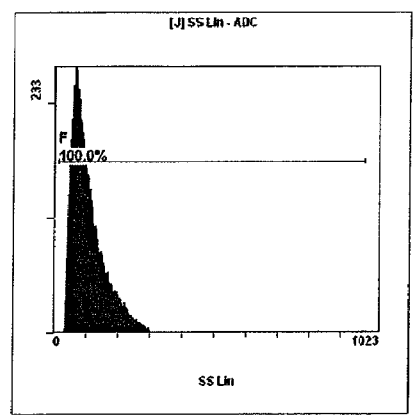
Figure 2:
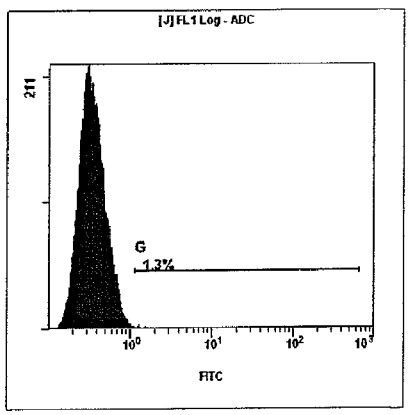
FIG. 2 shows flow cytometry data for quantification of CD34 in CBF cells.
Figure 2:
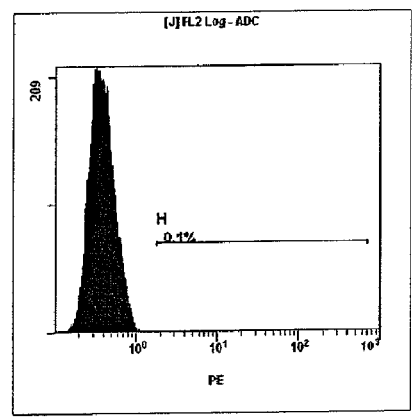
Figure 2:
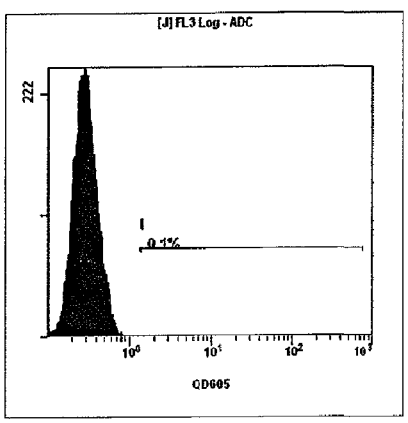
Figure 3:
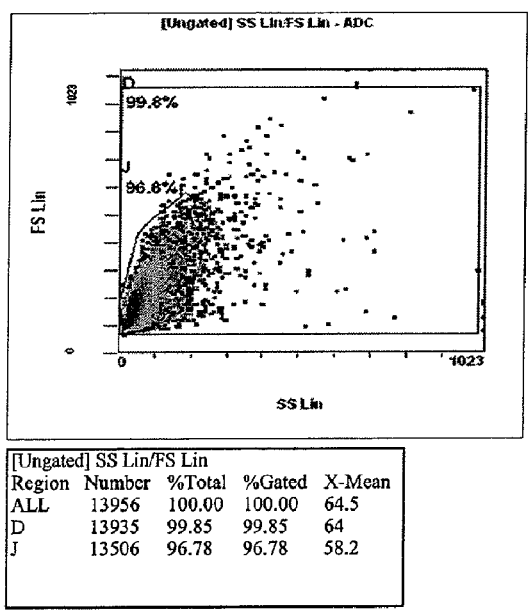
FIG. 3 shows flow cytometry data for quantification of CD34 in CBF cells.
Figure 3:
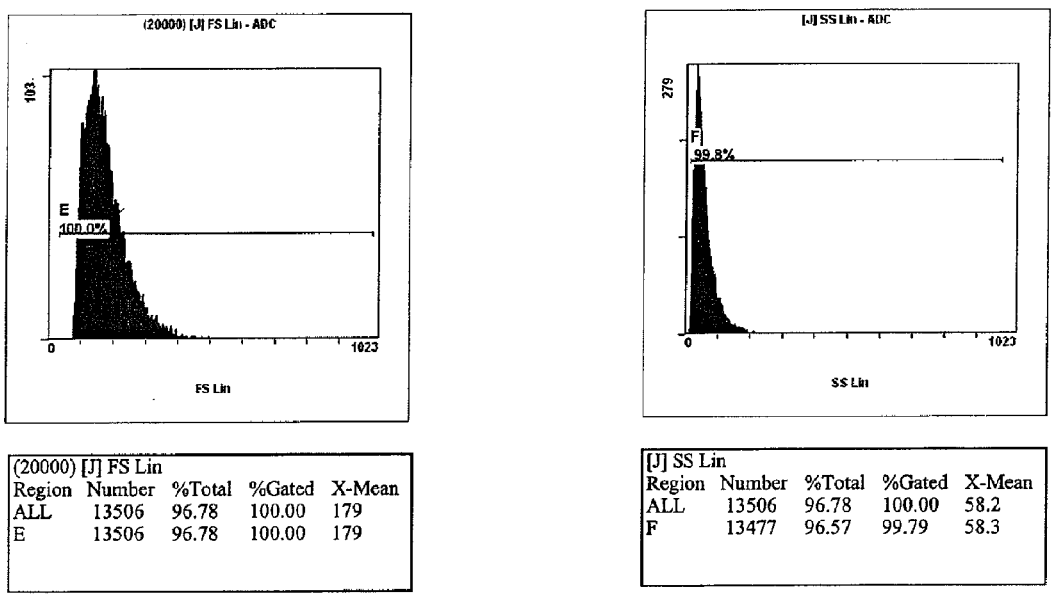
Figure 4:
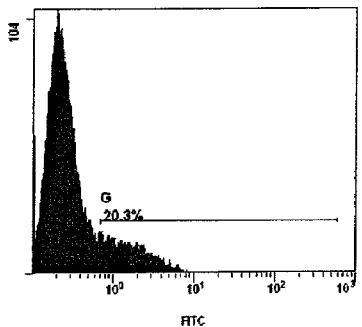
FIG. 4 shows flow cytometry data for quantification of CD34 in CBF cells.
Figure 4:
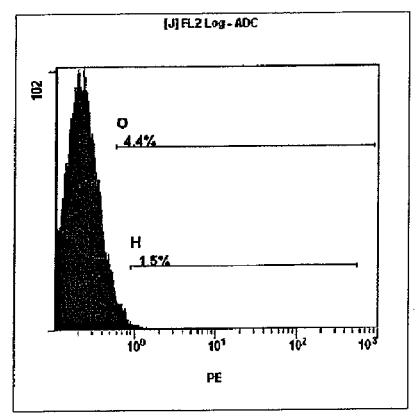
Figure 4:
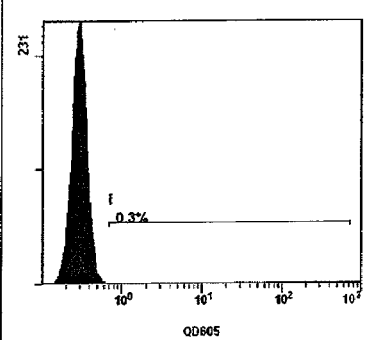
Figure 5:
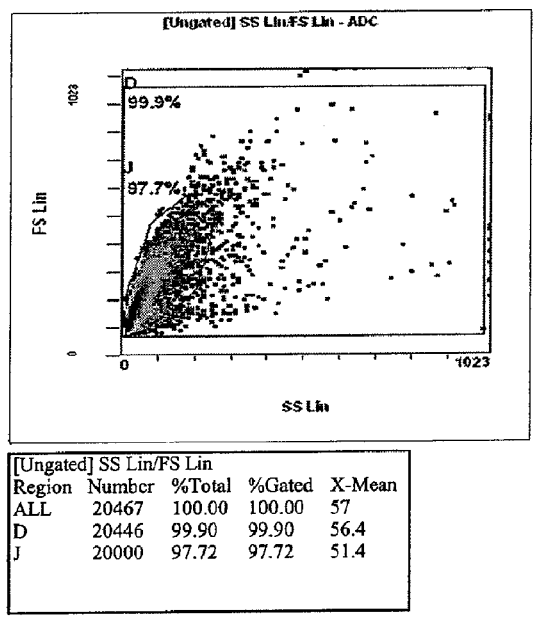
FIG. 5 shows flow cytometry data for quantification of CD34 in CBF cells.
Figure 5:
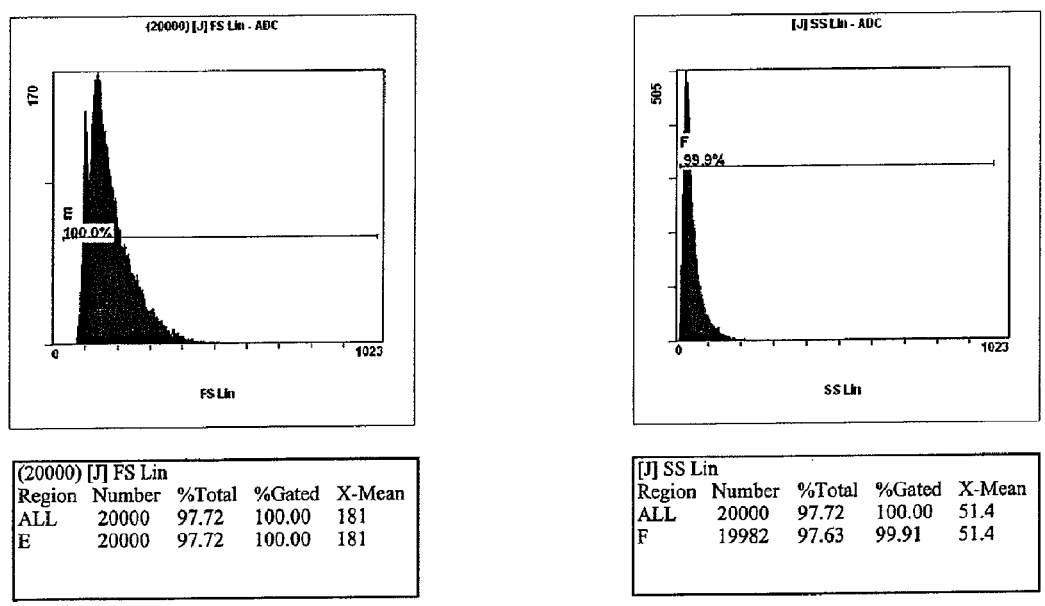
Figure 6:
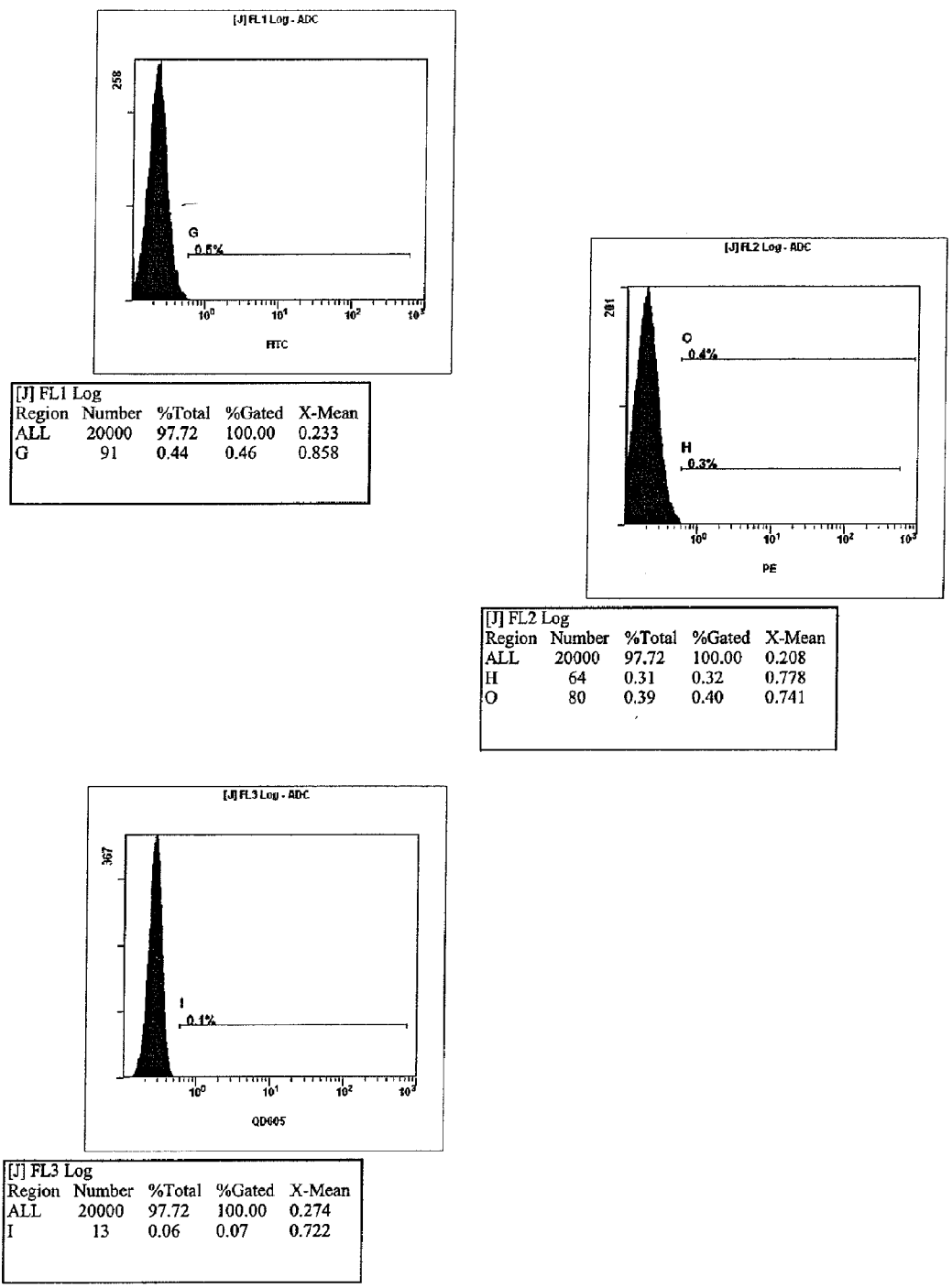
FIG. 6 shows flow cytometry data for quantification of CD34 in CBF cells.
Figure 7:
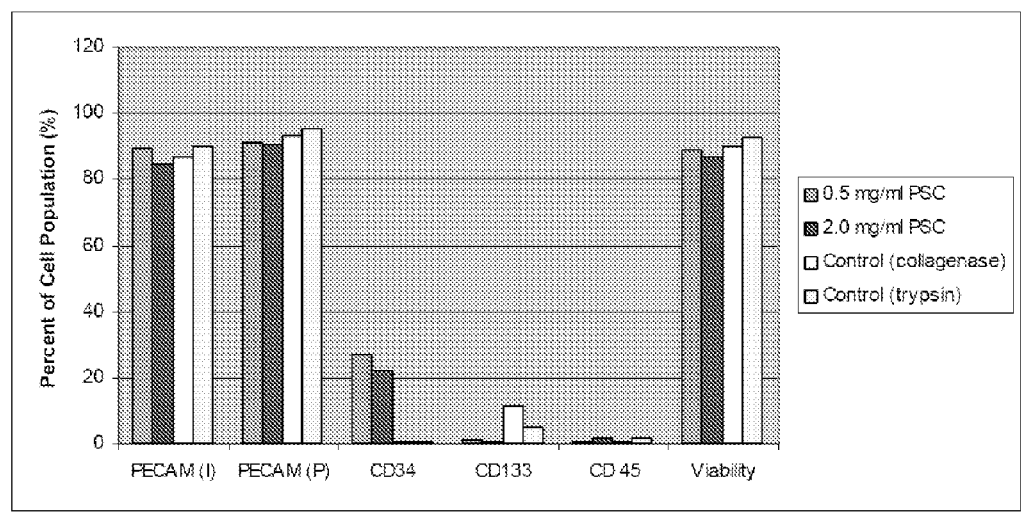
FIG. 7 shows a histogram of the percentage of cells expressing PECAM, CD34, CD133, and CD45 following harvest by collagenase cocktail or trypsin and 6 days in culture in 0.5 mg/ml or 2.0 mg/ml pig skin collagen (PSC) (within each group represented on the abscissa; the first bar from left=0.5 mg/ml PSC, second bar=2.0 mg/ml PSC, third bar=collagenase control, and fourth bar=trypsin control).

Methods and compositions for the support and differentiation of stem cells and for the formation of blood vessels and vascularized graft constructs are described. Applicants have developed and describe herein clinically-useful delivery strategies for rapid and effective vascularization of damaged or diseased tissues. The collagen-based matrices as herein described are useful, for example, for use as 1) 3D culture systems for expansion of stem/progenitor cells, 2) clinically relevant delivery vehicles for cell-based therapies, and 3) engineered tissue constructs with preformed vascular networks or enhanced capability for forming vascular networks in vivo.

In one embodiment, the engineered, purified collagen-based matrices are prepared by utilizing acid-solubilized type I collagen and defined polymerization (self-assembly) conditions that are controlled to yield 3D collagen extracellular matrices (ECMs) with a broad range of controlled assembly kinetics (e.g. polymerization half-time), molecular compositions, and fibril microstructure-mechanical properties, for example, as described in U.S. patent application Ser. No. 11/435,635 (published Nov. 22, 2007, as Publication No. 2007-0269476 A1) and Ser. No. 11/903,326 (published Oct. 30, 2008, as Publication No. 2008-0268052), each incorporated herein by reference.

Purified collagen can be obtained from a number of sources, including for example, porcine skin, to construct the engineered, purified collagen-based matrices described herein. Exemplary of tissues useful as a collagen-containing source material for isolating collagen to make the engineered, purified collagen-based matrices described herein are submucosa tissues or any other extracellular matrix-containing tissues of a warm-blooded vertebrate. Exemplary methods of preparing submucosa tissues are described in U.S. Pat. Nos. 4,902,508; 5,281,422; and 5,275,826, each incorporated herein by reference. Extracellular matrix material-containing tissues other than submucosa tissue may be used in accordance with the methods and compositions described herein. Methods of preparing other extracellular matrix material-derived tissues are known to those skilled in the art. For example, see U.S. Pat. No. 5,163,955 (pericardial tissue); U.S. Pat. No. 5,554,389 (urinary bladder submucosa tissue); U.S. Pat. No. 6,099,567 (stomach submucosa tissue); U.S. Pat. No. 6,576,265 (extracellular matrix tissues generally); U.S. Pat. No. 6,793,939 (liver basement membrane tissues); and U.S. patent application publication no. US-2005-0019419-A1 (liver basement membrane tissues); and international publication no. WO 2001/45765 (extracellular matrix tissues generally), each incorporated herein by reference. In various other embodiments, the collagen-containing source material can be selected from the group consisting of placental tissue, ovarian tissue, uterine tissue, animal tail tissue, and skin tissue. Any suitable extracellular matrix-containing tissue can be used as a collagen-containing source material.

An illustrative preparation method for preparing submucosa tissues as a source of collagen is described in U.S. Pat. No. 4,902,508, the disclosure of which is incorporated herein by reference. In one embodiment, a segment of vertebrate intestine, for example, preferably harvested from porcine, ovine or bovine species, but not excluding other species, is subjected to abrasion using a longitudinal wiping motion to remove cells or to cell-removal by hypotonic or hypertonic lysis. In this embodiment, the submucosa tissue is rinsed under hypotonic conditions, such as with water or with saline under hypotonic conditions and is optionally sterilized. In another illustrative embodiment, such compositions can be prepared by mechanically removing the luminal portion of the tunica mucosa and the external muscle layers and/or lysing resident cells with hypotonic or hypertonic washes, such as with water or saline. In these embodiments, the submucosa tissue can be stored in a hydrated or dehydrated state prior to extraction. In various aspects, the submucosa tissue can comprise any delamination embodiment, including the tunica submucosa delaminated from both the tunica muscularis and at least the luminal portion of the tunica mucosa of a warm-blooded vertebrate.

In various embodiments, the purified collagen can also contain glycoproteins, proteoglycans, glycosaminoglycans (e.g., chondroitins and heparins), etc. extracted from the insoluble fraction with the collagen. The engineered, purified collagen-based matrices prepared by the methods described herein can serve as matrices for the regrowth of endogenous tissues at the implantation site (e.g., biological remodeling) which can assume the characterizing features of the tissue(s) with which they are associated at the site of implantation, insertion, or injection.

In various illustrative embodiments, the collagen matrices, including an engineered matrix, can be disinfected and/or sterilized using conventional sterilization techniques including glutaraldehyde tanning, formaldehyde tanning at acidic pH, propylene oxide or ethylene oxide treatment, gas plasma sterilization, gamma radiation, electron beam, and/or peracetic acid sterilization. Sterilization techniques which do not adversely affect the structure and biotropic properties of the collagen can be used. Illustrative sterilization techniques are exposing the collagen-containing source material, the purified collagen, or the collagen-based matrix, including an engineered matrix, to peracetic acid, 1-4 Mrads gamma irradiation (or 1-2.5 Mrads of gamma irradiation), ethylene oxide treatment, or gas plasma sterilization. In one embodiment, the collagen-containing source material, the purified collagen, or the collagen-based matrix, including an engineered matrix, can be subjected to one or more sterilization processes. In an illustrative embodiment, peracetic acid can be used for sterilization.

Typically, prior to extraction, the collagen-containing source material is comminuted by tearing, cutting, grinding, or shearing the collagen-containing source material. In one illustrative embodiment, the collagen-containing source material can be comminuted by shearing in a high-speed blender, or by grinding the collagen-containing source material in a frozen state (e.g., at a temperature of −20° C., −40° C., −60° C., or −80° C. or below prior to or during the comminuting step) and then lyophilizing the material to produce a powder having particles ranging in size from about 0.1 mm$^2$ to about 1.0 mm$^2$. In one illustrative embodiment, the collagen-containing source material is comminuted by freezing and pulverizing under liquid nitrogen in an industrial blender. In this embodiment, the collagen-containing source material can be frozen in liquid nitrogen prior to, during, or prior to and during the comminuting step.

In one illustrative embodiment, after comminuting the collagen-containing source material, the material is mixed (e.g., by blending or stirring) with an extraction solution to extract and remove soluble proteins. Illustrative extraction solutions include sodium acetate (e.g., 0.5 M and 1.0 M). Other exemplary methods for extracting soluble proteins are known to those skilled in the art and are described in detail in U.S. Pat. No. 6,375,989, incorporated herein by reference. Illustrative extraction excipients include, for example, chaotropic agents such as urea, guanidine, sodium chloride or other neutral salt solutions, magnesium chloride, and non-ionic or ionic surfactants.

In one illustrative aspect, after the initial extraction, the soluble fraction can be separated from the insoluble fraction to obtain the insoluble fraction. For example, the insoluble fraction can be separated from the soluble fraction by centrifugation (e.g., 2000 rpm at 4° C. for 1 hour). In alternative embodiments, other separation techniques known to those skilled in the art, such as filtration, can be used. In one embodiment, the initial extraction step can be repeated one or more times, discarding the soluble fractions. In another embodiment, after completing the extractions, one or more steps can be performed of washing with water the insoluble fraction, followed by centrifugation, and discarding of the supernatant where the water is the supernatant.

In accordance with one illustrative embodiment, the insoluble fraction can then be extracted (e.g., with 0.075 M sodium citrate) to obtain the isolated collagen. In illustrative aspects the extraction step can be repeated multiple times retaining the soluble fractions. In one embodiment, the accumulated soluble fractions can be combined and can be clarified to form the soluble fraction, for example by centrifugation (e.g., 2000 rpm at 4° C. for 1 hour).

In one embodiment, the soluble fraction can be fractionated to precipitate the isolated collagen. In one illustrative aspect, the soluble fraction can be fractionated by dialysis. Exemplary molecular weight cut-offs for the dialysis tubing or membrane are from about 3,500 to about 12,000 or about 3,500 to about 5,000 or about 12,000 to about 14,000. In various illustrative embodiments, the fractionation, for example by dialysis, can be performed at about 2° C. to about 37° C. for about 1 hour to about 96 hours. In one embodiment, the soluble fraction is dialyzed against a buffered solution (e.g., 0.02 M sodium phosphate dibasic). However, the fractionation can be performed at any temperature, for any length of time, and against any suitable buffered solution. In one embodiment, the precipitated collagen is then collected by centrifugation (e.g., 2000 rpm at 4° C. for 1 hour). In another embodiment, after precipitation, one or more steps can be performed of washing the precipitate with water, followed by centrifugation, and discarding of the supernatant where the water is the supernatant.

In various illustrative embodiments, the precipitated collagen can then be resuspended in an aqueous solution wherein the aqueous solution is acidic. For example, the aqueous acidic solution can be an acetic acid solution, but any other acids including hydrochloric acid, formic acid, lactic acid, citric acid, sulfuric acid, ethanoic acid, carbonic acid, nitric acid, or phosphoric acid can be used. For example, acids, at concentrations of from about 0.001 N to about 0.1 N, from about 0.005 N to about 0.1 N, from about 0.01 N to about 0.1 N, from about 0.05 N to about 0.1 N, from about 0.001 N to about 0.05 N, from about 0.001 N to about 0.01 N, or from about 0.01 N to about 0.05 N can be used to resuspend the precipitate.

The term "lyophilized" means that water is removed from the composition, typically by freeze-drying under a vacuum. In one illustrative aspect, the isolated resuspended collagen can be lyophilized after it is resuspended. In another illustrative embodiment, the engineered matrix itself can be lyophilized. In one illustrative lyophilization embodiment, the resuspended collagen is first frozen, and then placed under a vacuum. In another lyophilization embodiment, the resuspended collagen can be freeze-dried under a vacuum. In another lyophilization embodiment, the precipitated collagen can be lyophilized before resuspension. Any method of lyophilization known to the skilled artisan can be used.

In additional embodiments, the acids described above can be used as adjuvants for storage after lyophilization in any combination. The acids that can be used as adjuvants for storage include hydrochloric acid, acetic acid, formic acid, lactic acid, citric acid, sulfuric acid, ethanoic acid, carbonic acid, nitric acid, or phosphoric acid, and these acids can be used at any of the above-described concentrations. In one illustrative embodiment, the lyophilizate can be stored (e.g., lyophilized in and stored in) an acid, such as acetic acid, at a concentration of from about 0.001 N to about 0.5 N or from about 0.01 N to about 0.5 N. In another embodiment, the lyophilizate can be stored in water with a pH of about 6 or below. In another embodiment, the lyophilized product can be stored dry. In other illustrative embodiments, lyoprotectants, cryoprotectants, lyophilization accelerators, or crystallizing excipients (e.g., ethanol, isopropanol, mannitol, trehalose, maltose, sucrose, tert-butanol, and tween 20), or combinations thereof, and the like can be present during lyophilization.

In accordance with one illustrative embodiment, the resuspended collagen is sterilized. Exemplary sterilizing and/or disinfecting agents are described above, but any sterilizing and/or disinfecting agent or method of sterilization known in the art can be used. The resuspended collagen can be sterilized using chloroform, glutaraldehyde, formaldehyde, acidic pH, propylene oxide, ethylene oxide, gas plasma sterilization, gamma radiation, electron beam sterilization, or peracetic acid sterilization, or combinations thereof, and the like. Illustrative sterilization techniques are exposing the resuspended collagen to peracetic acid, 1-4 Mrads gamma irradiation (or 1-2.5 Mrads of gamma irradiation), ethylene oxide treatment, or gas plasma sterilization.

In one embodiment, the isolated collagen can be sterilized before lyophilization. In another illustrative embodiment the isolated collagen can be sterilized after lyophilization or the collagen-containing source material can be sterilized. Sterilization of the collagen-containing source material can be performed, for example, as described in U.S. Pat. Nos. 4,902,508 and 6,206,931, incorporated herein by reference. In another illustrative embodiment, the polymerized matrix formed from the purified collagen is sterilized.

In one illustrative embodiment, the purified collagen is directly sterilized after resuspension, for example, with peracetic acid or with peracetic acid and ethanol (e.g., by the addition of 0.18% peracetic acid and 4.8% ethanol to the resuspended collagen solution before lyophilization). In another embodiment, sterilization can be carried out during the fractionation step. For example, the isolated collagen composition can be dialyzed against chloroform, peracetic acid, or a solution of peracetic acid and ethanol to disinfect or sterilize the isolated collagen. Illustratively, the isolated collagen can be sterilized by dialysis against a solution of peracetic acid and ethanol (e.g., 0.18% peracetic acid and 4.8% ethanol). The chloroform, peracetic acid, or peracetic acid/ethanol can be removed prior to lyophilization, for example by dialysis against an acid, such as 0.01 N acetic acid. In an alternative embodiment, the lyophilized composition can be sterilized directly after rehydration, for example, by the addition of 0.18% peracetic acid and 4.8% ethanol. In this embodiment, the sterilizing agent can be removed prior to polymerization of the purified collagen to form fibrils.

If the purified collagen or polymerized collagen is lyophilized, the lyophilized composition can be stored frozen, refrigerated, or at room temperature (for example, at about −80° C. to about 25° C.). Storage temperatures are selected to stabilize the collagen. The compositions can be stored for about 1-26 weeks, or longer.

In one embodiment, the purified collagen can be dialyzed against 0.01 N acetic acid, for example, prior to lyophilization to remove the sterilization solution and so that the purified collagen is in a 0.01 N acetic acid solution. In another embodiment, the purified collagen can be dialyzed against hydrochloric acid, for example, prior to lyophilization and can be lyophilized in hydrochloric acid and redissolved in hydrochloric acid, acetic acid, or water.

If the purified collagen is lyophilized, the resulting lyophilizate can be redissolved in any solution, but may be redissolved in an acidic solution or water. In various aspects, the lyophilizate can be redissolved in, for example, acetic acid, hydrochloric acid, formic acid, lactic acid, citric acid, sulfuric acid, ethanoic acid, carbonic acid, nitric acid, or phosphoric acid, at any of the above-described concentrations, or can be redissolved in water. In one illustrative embodiment the lyophilizate is redissolved in 0.01 N acetic acid.

For use in producing engineered matrices that can be injected or implanted in vivo or used for other purposes in vitro, the redissolved lyophilizate can be subjected to varying conditions (e.g., pH, phosphate concentration, temperature, buffer composition, ionic strength, and composition and concentration of the purified collagen components (dry weight/ml)) that result in polymerization to form engineered matrices with specific characteristics.

In illustrative embodiments, as discussed above, the polymerization reaction for engineered matrices can be conducted in a buffered solution using any biologically compatible buffer system known to those skilled in the art. For example, the buffer may be selected from the group consisting of phosphate buffer saline (PBS), Tris (hydroxymethyl)aminomethane Hydrochloride (Tris-HCl), 3-(N-Morpholino) Propanesulfonic Acid (MOPS), piperazine-n,n'-bis(2-ethanesulfonic acid) (PIPES), [n-(2-Acetamido)]-2-Aminoethanesulfonic Acid (ACES), N-[2-hydroxyethyl]piperazine-N'-[2-ethanesulfonic acid] (HEPES) and 1,3-bis[tris (Hydroxymethyl)methylamino]propane (Bis Tris Propane). In one embodiment the buffer is PBS, Tris, or MOPS and in one embodiment the buffer system is PBS, and more particularly 10×PBS. In accordance with one embodiment, the 10×PBS buffer at pH 7.4 comprises the following ingredients:

1.37 M NaCl
0.027 M KCl
0.081 M Na$_2$HPO$_4$
0.015 M KH$_2$PO$_4$
5 mM MgCl$_2$
55.5 mM glucose All of the conditions that can be varied to polymerize and engineer the collagen matrices described herein (e.g., pH, phosphate concentration, temperature, buffer composition, ionic strength, and composition and concentration of the purified collagen components (dry weight/ml)) are described in U.S. application Ser. No. 11/903,326 (published Oct. 30, 2008, as Publication No. 2008-0268052), incorporated herein by reference. The tissue graft constructs that are formed from the engineered, purified collagen-based matrices described herein can be injected or implanted, or, for example, applied topically to wounds, all by methods known to those skilled in the art.

The purified collagen is derived from a collagen-containing source material and, in some embodiments, may contain glycoproteins, such as laminin and fibronectin, proteoglycans, such as serglycin, versican, decorin, and perlecan, and glycosaminoglycans. In one embodiment, the purified collagen can be further purified or partially purified and the purified or partially purified composition can be used in accordance with the methods described herein or mixtures of partially purified or purified components can be used. As used herein, the term "purified" means the isolation of collagen in a form that is substantially free from other components (e.g., typically the total amount of other components present in the composition represents less than 5%, or more typically less than 0.1%, of total dry weight).

As discussed, the collagen-based matrices as herein described may be made under controlled conditions to obtain particular mechanical properties. For example, the collagen-based matrices described may have desired collagen fibril density, pore size (fibril-fibril branching), elastic modulus, tensile strain, tensile stress, linear modulus, compressive modulus, loss modulus, fibril area fraction, fibril volume fraction, collagen concentration, cell seeding density, shear storage modulus (G' or elastic (solid-like) behavior), and phase angle delta (δ or the measure of the fluid (viscous)- to solid (elastic)-like behavior; δ equals 0° for Hookean solid and 90° for Newtonian fluid).

As used herein, a "modulus" can be an elastic or linear modulus (defined by the slope of the linear region of the stress-strain curve obtained using conventional mechanical testing protocols; i.e., stiffness), a compressive modulus, a loss modulus, or a shear storage modulus (e.g., a storage modulus). These terms are well-known to those skilled in the art.

As used herein, a "fibril volume fraction" is defined as the percent area of the total area occupied by fibrils in 3 dimensions.

As used herein, tensile or compressive stress "σ" is the force carried per unit of area and is expressed by the equation:

$$\sigma = \frac{P}{A} = \frac{P}{ab}$$

where:
  s=stress
  P=force
  A=cross-sectional area
  a=width
  h=height

The force (P) produces stresses normal (i.e., perpendicular) to the cross section of the part (e.g., if the stress tends to lengthen the part, it is called tensile stress, and if the stress tends to shorten the part, it is called compressive stress).

As used herein, "tensile strain" is the strain caused by bending and/or stretching a material.

In one embodiment, the fibril volume fraction of the matrix is about 1% to about 60%. In various embodiments, the collagen-based matrix can contain fibrils with specific characteristics, for example, a fibril volume fraction (i.e., density) of about 2% to about 60%, about 2% to about 40%, about 5% to about 60%, about 15% to about 60%, about 5% to about 40%, about 1% to about 50%, about 1% to about 40%, about 1% to about 30%, about 1% to about 20%, about 1% to about 15%, about 1% to about 10%, about 1% to about 5%, about 5% to about 20%, about 5% to about 50%, about 20% to about 60%, about 30% to about 50%, about 30% to about 60%, about 50% to about 60%, about 1% to about 2%, about 1% to about 3%, and about 1% to about 4%. In various illustrative embodiments, the fibril volume fraction is about 1%, about 5%, about 10%, about 15%, about 20%, about 25%, about 30%, about 40%, about 50%, or about 60%.

In other illustrative embodiments, the collagen-based matrix can contain fibrils with specific characteristics, including, but not limited to, a modulus (e.g., a compressive modulus, loss modulus, or a storage modulus) of about 1 Pa to about 75 Pa, about 10 Pa to about 700 Pa, about 2500 Pa to about 18,000 Pa, about 10 Pa to about 75 Pa, about 1 Pa to about 700 Pa, about 10 Pa to about 10,000 Pa, and about 1 Pa to about 18,000 Pa.

In another embodiment, the collagen-based matrix can contain fibrils with specific characteristics, including, but not limited to, a storage modulus of about 10 Pa to about 700 Pa. In another illustrative embodiment, the storage modulus of the matrix is about 10 Pa to about 600 Pa, about 10 Pa to about 500 Pa, about 10 Pa to about 250 Pa, about 40 Pa to about 50 Pa, about 50 Pa to about 700 Pa, about 50 Pa to about 500 Pa, about 100 Pa to about 700 Pa, about 100 Pa to about 500 Pa, about 100 Pa to about 250 Pa, about 200 Pa to about 700 Pa, about 500 Pa to about 700 Pa, and about 650 Pa to about 700 Pa.

In yet another embodiment, the collagen-based matrix can contain fibrils with specific characteristics, including, but not limited to, a loss modulus of about 1 Pa to about 75 Pa. In another illustrative embodiment, the loss modulus of the matrix is about 1 Pa to about 60 Pa, about 1 Pa to about 50 Pa, about 1 Pa to about 40 Pa, about 1 Pa to about 30 Pa, about 1 Pa to about 25 Pa, about 1 Pa to about 20 Pa, about 1 Pa to about 10 Pa, about 2 Pa to about 70, about 2 Pa to about 50 Pa, about 5 Pa to about 70 Pa, about 5 Pa to about 50 Pa, about 5 Pa to about 30 Pa, about 5 Pa to about 25 Pa, about 10 Pa to about 70 Pa, and about 10 Pa to about 50 Pa.

In a further embodiment, the collagen-based matrix can contain fibrils with specific characteristics, including, but not limited to, a compressive modulus of about 2500 Pa to about 18,000 Pa. In another illustrative embodiment, the compressive modulus of the matrix is about 2500 to about 15,000, about 2500 to about 10,000, about 5000 to about 10,000, about 5000 to about 12,000, about 5000 to about 15,000, and about 5000 to about 18,000.

In another embodiment, the composition comprises one or more vessels. In one embodiment, the blood vessels are produced de novo. In another embodiment, methods for promoting vessel formation within a tissue graft are described. In this embodiment, the method comprises the steps of engineering a purified collagen-based matrix comprising collagen fibrils, and contacting the matrix with endothelial progenitor cells, wherein one or more vessels are formed within the matrix. In another embodiment, the one or more vessels are isolated from the matrix. In yet another embodiment, the isolated one or more vessels are implanted into the tissue of a patient, using methods known in the art. The isolated vessels may be used for the treatment of various disease states as herein described. In another embodiment, a method of forming vessels in vivo is provided. The method comprises the step of implanting an engineered, purified collagen-based matrix comprising collagen fibrils and endothelial progenitor cells into a patient wherein vessel formation at the implantation site is enhanced in vivo. The enhancement can be in comparison to implantation of a matrix without cells.

In another embodiment, methods are described for the treatment of a patient. For example, a patient may be treated wherein the tissue of the patient is in need of vascularization. The method comprises the steps of engineering a purified collagen-based matrix comprising collagen fibrils, contacting the matrix with endothelial progenitor cells wherein vessels are formed de novo, isolating the vessels from the matrix, and implanting the vessels into the tissue of the patient. Exemplary disease states or injuries to be treated using the compositions and methods described herein include, for example, complications associated with diabetes, peripheral vascular disease, cerebral ischemia, cardiovascular disease (e.g. coronary artery disease), and for wound healing, including the treatment of wounds in a burn patient (e.g., to increase the rate of revascularization), treatment to reduce or prevent scarring and stricture formation, and the treatment of wounds in a diabetic patient (e.g., to treat limb ischemia or diabetic ulcers).

In various embodiments, the collagen can also contain glycoproteins, proteoglycans, glycosaminoglycans (e.g., chondroitins and heparins), etc. extracted from the insoluble fraction with the collagen. The engineered matrices prepared by the methods described herein can serve as matrices for the regrowth of endogenous tissues at the implantation site (e.g., biological remodeling) which can assume the characterizing features of the tissue(s) with which they are associated at the site of implantation, insertion, or injection.

In various illustrative embodiments, qualitative and quantitative microstructural characteristics of the engineered matrices can be determined by environmental or cryostage scanning electron microscopy, transmission electron microscopy, confocal microscopy, second harmonic generation multi-photon microscopy. In another embodiment, polymerization kinetics may be determined by spectrophotometry or time-lapse confocal reflection microscopy. In another embodiment, tensile, compressive and viscoelastic properties can be determined by rheometry or tensile testing. In another embodiment, a rat subcutaneous injection model can be used to determine remodeling properties. All of these methods are known in the art or are further described in U.S. patent application Ser. No. 11/435,635 (published Nov. 22, 2007, as Publication No. 2007-0269476 A1), or are described in Roeder et al., *J. Biomech. Eng.*, vol. 124, pp. 214-222 (2002), in Pizzo et al., *J. Appl. Physiol.*, vol. 98, pp. 1-13 (2004), Fulzele et al., *Eur. J. Pharm. Sci.*, vol. 20, pp. 53-61 (2003), Griffey et al., *J. Biomed. Mater. Res.*, vol. 58, pp. 10-15 (2001), Hunt et al., *Am. J. Surg.*, vol. 114, pp. 302-307 (1967), and Schilling et al., *Surgery*, vol. 46, pp. 702-710 (1959), incorporated herein by reference.

Typically, the matrices are prepared from isolated collagen at collagen concentrations ranging from about 0.05 mg/ml to about 5.0 mg/ml, about 1.0 mg/ml to about 3.0 mg/ml, about 0.05 mg/ml to about 10 mg/ml, about 0.05 to about 20 mg/ml, about 0.05 mg/ml to about 3.0 mg/ml, about 0.3 to about 1 mg/ml, about 0.3 to about 1.5 mg/ml, about 0.3 mg/ml to about 5 mg/ml, about 0.75 mg/ml to about 5 mg/ml, about 1 mg/ml to about 5 mg/ml, about 1 mg/ml to about 2 mg/ml, about 1 mg/ml to about 3 mg/ml, about 1 mg/ml to about 4 mg/ml, about 1.5 mg/ml to about 5 mg/ml, and about 1.5 mg/ml to about 3 mg/ml. In various illustrative embodiments, the collagen concentration is about 0.3 mg/ml, about 0.5 mg/ml, about 0.75 mg/ml, about 1.0 mg/ml, about 1.5 mg/ml, about 2.0 mg/ml, about 3.0 mg/ml, or about 5.0 mg/ml.

In any of these embodiments the engineered graft construct may further comprise an added population of cells. The added population of cells may comprise one or more cell populations. In various embodiments, the cell populations comprise a population of mesodermally derived cells selected from the group consisting of endothelial cells, neural cells, pericytes, osteoblasts, fibroblasts, smooth muscle cells, skeletal muscle cells, cardiac muscle cells, mesenchymal cells, adipocytes, adipose stromal cells, progenitor cells (e.g., stem cells, including bone marrow progenitor cells), unrestricted somatic stem cells (USSCs), endothelial progenitor cells (EPCs), endothelial colony forming cells (ECFCs), and osteogenic cells. In various embodiments, the collagen matrix can be seeded with one or more cell types in combination.

In one embodiment, a source of cells suitable to form vascular networks are endothelial progenitor cells (EPCs). EPCs are released into the circulation of a patient and home to sites of vessel formation in both physiological and pathological settings. EPCs integrate into injured or disease sites including tumors, ischemic skeletal and cardiac muscle, and ulcers.

As used herein, "stem cell" refers to an unspecialized cell from an embryo, fetus, or adult that is capable of self-replication or self-renewal and can develop into specialized cell types of a variety of tissues and organs (i.e., potency). The term as used herein, unless further specified, encompasses totipotent cells (those cells having the capacity to differentiate into extra-embryonic membranes and tissues, the embryo, and all post-embryonic tissues and organs), pluripotent cells (those cells that can differentiate into cells derived from any of the three germ layers), multipotent cells (those cells having the capacity to differentiate into a limited range of differentiated cell types, e.g., mesenchymal stem cells, adipose-derived stem cells, endothelial stem cells, etc.), oligopotent cells (those cells that can differentiate into only a few cell types, e.g., lymphoid or myeloid stem cells), and unipotent cells (those cells that can differentiate into only one cell type, e.g., muscle stem cells). Stem cells may be isolated from, for example, circulating blood, umbilical cord blood, or bone marrow by methods well-known to those skilled in the art.

Examples of progenitor cells include those that give rise to blood cells, fibroblasts, endothelial cells, epithelial cells, smooth muscle cells, skeletal muscle cells, cardiac muscle cells, multi-potential progenitor cells, pericytes, and osteogenic cells. The population of progenitor cells can be selected based on the cell type of the intended tissue to be repaired. For example, if skin is to be repaired, the population of progenitor cells will give rise to non-keratinized epithelial cells or if cardiac tissue is to be repaired, the progenitor cells can produce cardiac muscle cells. The matrix composition can also be seeded with autogenous cells isolated from the patient to be treated. In an alternative embodiment the cells may be xenogeneic or allogeneic in nature.

In accordance with one embodiment the stem cells are seeded within the collagen-based matrix at a cell density of about $1 \times 10^6$ to about $1 \times 10^8$ cells/ml, or at a density of about $1 \times 10^3$ to about $2 \times 10^6$ cells/ml. In one embodiment stem cells are seeded at a density of less than $5 \times 10^4$ cells/ml, more typically at a density of about $5 \times 10^4$ cells/ml. In another embodiment cells are seeded at a density of less than $1 \times 10^4$ cells/ml. In another embodiment, cells are seeded at a density selected from a range of about $1 \times 10^2$ to about $5 \times 10^6$, about $0.3 \times 10^4$ to about $60 \times 10^4$ cells/ml, and about $0.5 \times 10^4$ to about $50 \times 10^4$ cells/ml. In various illustrative embodiments, the cells are seeded at a density of about $0.3 \times 10^4$ cells/ml, about $5 \times 10^4$ cells/ml, about $10 \times 10^4$ cells/ml, about $20 \times 10^4$ cells/ml, about $40 \times 10^4$ cells/ml, $60 \times 10^4$ cells/ml, and $1 \times 10^5$, about $5 \times 10^5$, about $1 \times 10^6$ cells/ml, and about $2 \times 10^6$ cells/ml. The cells are maintained or differentiated according to methods described herein or to methods well-known to the skilled artisan for cell culture.

In various embodiments, the engineered matrices of the present invention can be combined, prior to, during, or after polymerization, with nutrients, including minerals, amino acids, sugars, peptides, proteins, vitamins (such as ascorbic acid), or glycoproteins that facilitate cellular proliferation, such as laminin and fibronectin, hyaluronic acid, or growth factors such as epidermal growth factor, platelet-derived growth factor, transforming growth factor beta, or fibroblast growth factor, and glucocorticoids such as dexamethasone. In other illustrative embodiments, fibrillogenesis inhibitors, such as glycerol, glucose, or polyhydroxylated compounds can be added prior to or during polymerization. In accordance with one embodiment, cells can be added to the isolated collagen as the last step prior to the polymerization or after polymerization of the engineered matrix. In other illustrative embodiments, cross-linking agents, such as carbodiimides, aldehydes, lysl-oxidase, N-hydroxysuccinimide esters, imidoesters, hydrazides, and maleimides, and the like can be added before, during, or after polymerization.

In another embodiment, the cells are isolated form the matrix using an enzyme. For example, stem cells are isolated from the matrix using collagenase or a solution thereof. Additional enzymes useful for isolation of cells from the matrix include, for example, proteases such as serine proteases, thiol proteases, and metalloproteinases, including the matrix metalloproteinases such as the collagenases, gelatinases, stromelysins, and membrane type metalloproteinase, or combinations thereof.

In various illustrative embodiments, the collagen used herein may be any type of collagen, including collagen types I to XXVIII, alone or in any combination. The collagen-based matrices prepared by the methods described herein can serve as compositions for the isolation, expansion, production, and transplantation of cells and vessels.

In another embodiment, endothelial progenitor cells can be used (e.g., to form vessels) or to generate a population of stem cells (e.g., cells expressing CD34). In one embodiment, a method is described for enhancing CD34 expression on cells. The method comprises the steps of engineering a purified collagen-based matrix comprising collagen fibrils, and contacting the matrix with endothelial progenitor cells, wherein the cells exhibit enhanced CD34 expression.

Any cell marker can be used to select and purify the cell type desired. For example, suitable markers for the selection and purification of endothelial progenitor cells include, but are not limited to, CD34, CD 133, CD31, VE-Cadherin, VEGFR2, c-kit, CD45, and Tie-2. Additionally, several markers are expressed by both early angioblasts and hematopoietic elements including CD31 (PECAM—platelet endothelial cell adhesion molecule), CD34 (a general stem and progenitor cell marker), and vascular endothelial growth factor receptor type 2 (VEGFR-2 also called KDR/Flk-1). Cell markers may be used alone or in combination to select and purify the desired cell type for use in the compositions and methods herein described.

In one embodiment, EPCs with a high proliferation capacity, otherwise known as ECFCs, are suspended in a liquid-phase, injectable collagen formulation designed to polymerize in situ to form a 3D matrix. The delivery system comprises soluble collagen, for example, soluble type I collagen, and defined polymerization reaction conditions yield natural polymeric matrices with controlled molecular composition, fibril microstructure, and mechanical properties (e.g., stiffness), for example. Systematically varying both matrix stiffness and fibril density of the matrix predictably modulates ECFC vessel formation in vivo. Vascular networks by EPCs in vivo and in vitro as described can be modulated by precision-tuning specific fibril microstructure and viscoelastic parameters of the matrices, for example, the fibril density, pore size (fibril-fibril branching), shear storage modulus (G' or elastic (solid-like) behavior), and phase angle delta ($\delta$ or the measure of the fluid (viscous)- to solid (elastic)-like behavior; $\delta$ equals 0° for Hookean solid and 90° for Newtonian fluid).

Applicants have developed type I collagen formulations derived from various collagen sources, e.g., pig skin. These formulations comprise both type I collagen monomers (single triple helical molecules) and oligomers (at least two monomers covalently crosslinked together). The presence of oligomers enhances the self-assembly potential by increasing the assembly rate and by yielding 3D matrices with distinct fibril microstructures and increased mechanical integrity (e.g., stiffness). These collagen-based matrix formulations, together with defined polymerization conditions, are controlled to reproducibly yield 3D matrices with a range of tunable assembly kinetics (e.g. polymerization half-time), molecular compositions, and fibril microstructure-mechanical properties.

Modulation of specific biophysical parameters of a collagen-based matrix as described, specifically fibril microstructure (length, diameter, and pore-size (fibril-fibril branching)) and mechanical properties (e.g., stiffness), regulates the fundamental behavior of resident cells. For example, multi-potential human mesenchymal stem cells entrapped within a 3D collagen matrix characterized by a relatively high fibril density and stiffness (G') show enhanced osteogenesis (bone formation), while those in a low fibril density and stiffness matrix show enhanced adipogenesis (fat formation). ECFCs grown within collagen matrices in vitro show impressive vascular networks whose properties can be modulated by varying specific fibril microstructure-mechanical design parameters of the matrix as herein described.

The following examples illustrate specific embodiments in further detail. These examples are provided for illustrative purposes only and should not be construed as limiting the invention or the inventive concept in any way.

Example 1

Variation of Microstructure-Mechanical Properties of Component Collagen Fibrils within a 3D Collagen ECM Modulated Mesenchymal Cell Shape and Cytoskeletal Organization Results showed that variation of microstructure-mechanical properties of component collagen fibrils within a 3D collagen ECM modulated mesenchymal cell (MSC) shape and cytoskeletal organization. In addition, such alteration was sufficient to direct distinct growth and lineage-specific differentiation patterns of resident MSCs. Such signaling via the local 3D collagen fibril microstructure and mechanical properties occurred for MSCs cultured in "regular" medium and did not require a specialized cocktail of soluble factors. Specifically, MSCs seeded within ECMs with a fibril density of 20% and storage modulus of 44.64±8.03 Pa readily proliferated and developed a mixed cell population including adipocytes and presumably undifferentiated, spindle-shaped cells. In contrast, MSCs seeded within ECMs with a fibril density of 55% and a storage modulus of 694.05±53.09 Pa proliferated less and developed a different combination of cell types including minimal to no adipocytes, a decreased number of spindle-shaped cells, and focal aggregates of osteoblasts.

Real time RT-PCR data for LPL and CBFA1 corroborated morphology and histochemical staining results. Incubation of the constructs in the presence of "adipogenic" medium exaggerated these ECM-dependent results. There was a 9-fold increase in the number of adipocytes observed within constructs after 14 days of culture within low fibril density/stiffness ECMs in the presence of "adipogenic" medium. In contrast, MSCs cultured in high fibril density/stiffness ECMs in the presence of "adipogenic" medium showed only a moderate increase in adipogenic differentiation (approximately 2 times) but an 8-fold increase in the number of calcified bone nodules.

Example 2

Differentiation Potential

Follow-up studies were conducted to determine if the initial seeding density affected the proliferative and lineage specific differentiation potential of MSCs within 3D engineered ECMs. MSCs were seeded in high fibril density/stiffness ECMs at densities ranging from $0.5 \times 10^4$ cells/ml to $50 \times 10^4$ cells/ml and the constructs again maintained in either "regular" or "adipogenic" media. In general, decreasing the cell seeding density caused a decrease in cell-cell interactions, an increase in cell-ECM interactions, a decrease in adipogenesis, and an increase in osteogenesis, despite the culture medium. When seeded at a low cell density, MSCs grew as focal regions, which expressed osteogenic phenotype and function, with little to no evidence of other cell types. As the initial seeding density was increased, a cell population of mixed phenotypes developed. At the highest cell density, adipocytes and undifferentiated MSCs were prominent with no evidence of osteogenesis.

The methods and compositions described herein assist in the definition of design criteria for the development of "instructive", self-assembled, collagen-based 3D ECMs that can predictably control cell behavior and contribute to the development of functional tissues and organs for clinical applications.

Example 3

Expression of Cell Surface Markers

CBFs were brought out of freezing and briefly cultured on plastic. At t=0, cells were harvested and a subset of the cells were 1) seeded within 3D ECMs; 2) seeded on plastic; or 3) subjected to flow cytometry analysis to establish t=0 results; cells were analyzed for expression of cell surface markers CD34, CD133, and PECAM; control samples representing "Cells only" and "2ndary antibody control (PECAM only)" were also analyzed. On day 6 (t=6 days), cells seeded within 3D ECM and seeded on plastic were harvested and analyzed by flow cytometry (same cell surface markers and controls were included as part of this analysis). A summary of results is provided in Table 1. CD34 expression increased for cells cultured on ECMs.

TABLE 2

|  | Plastic-PS (t = 0) | ECM (t = 6 days) | Plastic-PS (t = 6 days) | Plastic-PureCol (t = 6 days) |
|---|---|---|---|---|
| CD 34 | 1.3 | 20.3 | 0.5 | 0.1 |
| PECAM | 94.4 | 96.7 | 95.6 | 97.7 |
| CD 133 | 16.6* | 3.5 | 0.4 | 0.2 |
| 2° Ab Control (PECAM) | 0.2 | 2.4 | 1.5 | 1.1 |

Note:
Results based upon preliminary gate setting; gates set such that results obtained for cells only control were <1.3%

Example 4

Flow Cytometric Analysis

Endothelial progenitor cells (EPCs; passage 9) were seeded at cell densities of $1\times10^5$ cells/ml within 3D ECMs polymerized at 0.5 mg/ml (fibril density of 6% and storage modulus of 44.64±8.03 Pa) and 2.0 mg/ml (fibril density of 16% and a storage modulus of 694.05±53.09 Pa) pig skin type I collagen. After 6 days of culture, cells were harvested from the ECMs using a collagenase cocktail (see Example 7). The cells then were immunofluorescently labeled for PECAM, CD34, CD133, and CD45 and analyzed using flow cytometry (see FIGS. 1-7). The initial cell population, which was propagated on plastic, was harvested using either the collagenase or standard trypsin method and served as controls. Recovery of cells from the 0.5 mg/ml and 2.0 mg/ml ECMs was calculated at 26.5% and 21.2%, respectively. The cells grown on ECMs showed increased CD34 expression.

Figure 23:
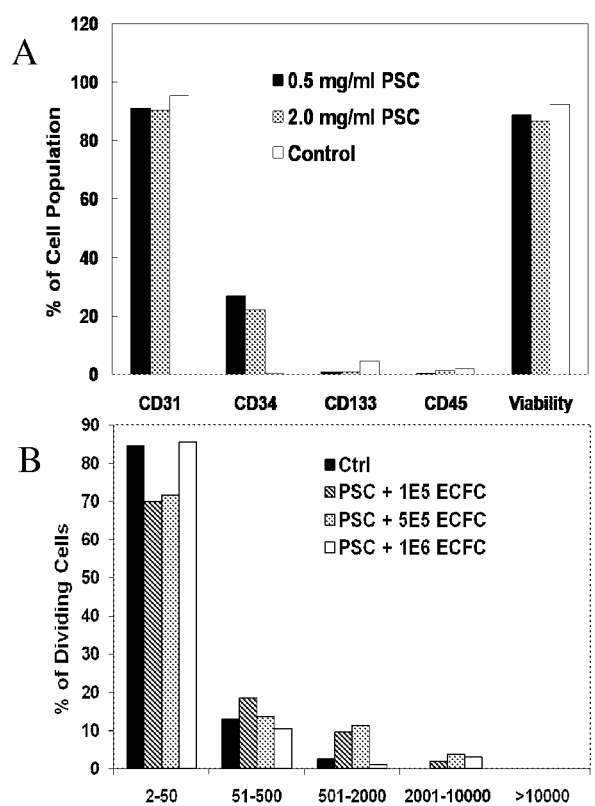
FIG. 23 shows the modulation of cell surface marker expression for ECFCs cultured in vitro (6 days) within collagen matrices of varied fibril density and stiffness compared to the initial ECFC population (Control) (Panel A). Panel B shows the modulation of colony forming potential for ECFCs cultured in vitro (6 days) within collagen matrices at different seeding densities compared to the initial ECFC population (Control).

Flow cytometric analysis of the total cell population following extraction from the 3D matrix shows an intriguing shift in cell surface marker expression compared to the initial ECFC population (FIG. 23, Panel A). Specifically, the number of cells expressing CD34 increases while the number of cells expressing CD133 decreases compared to the initial population. Furthermore, expression of CD31 remains high while there is no evidence of expression of CD45, a marker specific for hematopoietic cells. In addition, the cells harvested from the matrix show a distinct shift in their proliferative potential (FIG. 23, Panel B). The differences show an increase in the number of mature endothelial cells showing low proliferative potential and an emerging small subpopulation showing enhanced proliferative potential compared to the initial ECFC population.

Example 5

Endothelial Progenitor Cells (EPCS)

Figure 8:
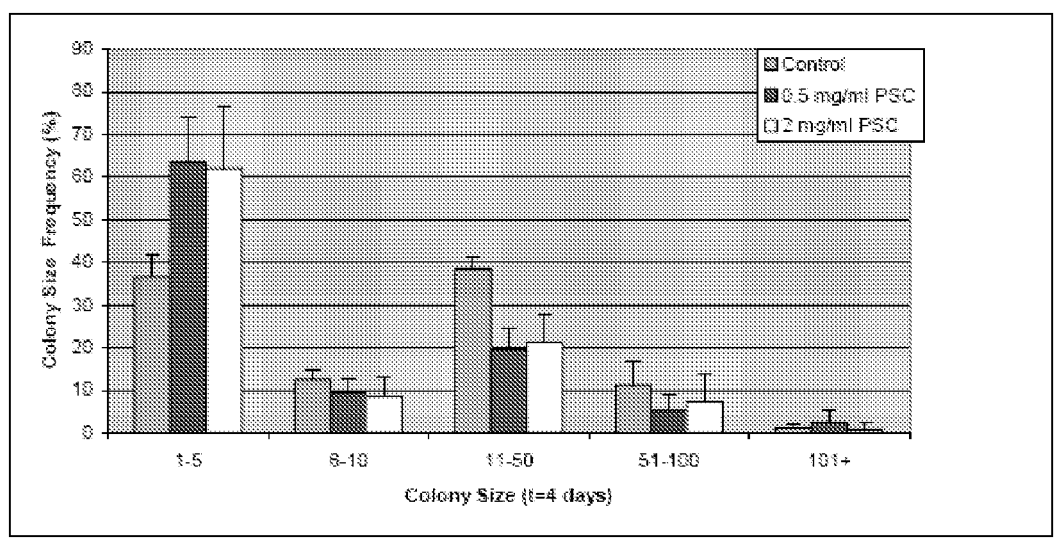
FIG. 8 shows a histogram of the colony size formed (t=4 days) by an endothelial progenitor cell (EPC) population before being seeded within 3D ECMs (Ctrl) and after being seeded at cell densities of $1\times10^5$ cells/ml within 3D ECMs polymerized at 0.5 mg/ml and 2.0 mg/ml PSC. Note the shift in the colony forming potential for the cells seeded under the different conditions. These data include single cell events. (within each group represented on the abscissa; the left bar=control, middle bar=0.5 mg/ml PSC, right bar=2 mg/ml PSC).
Figure 9:
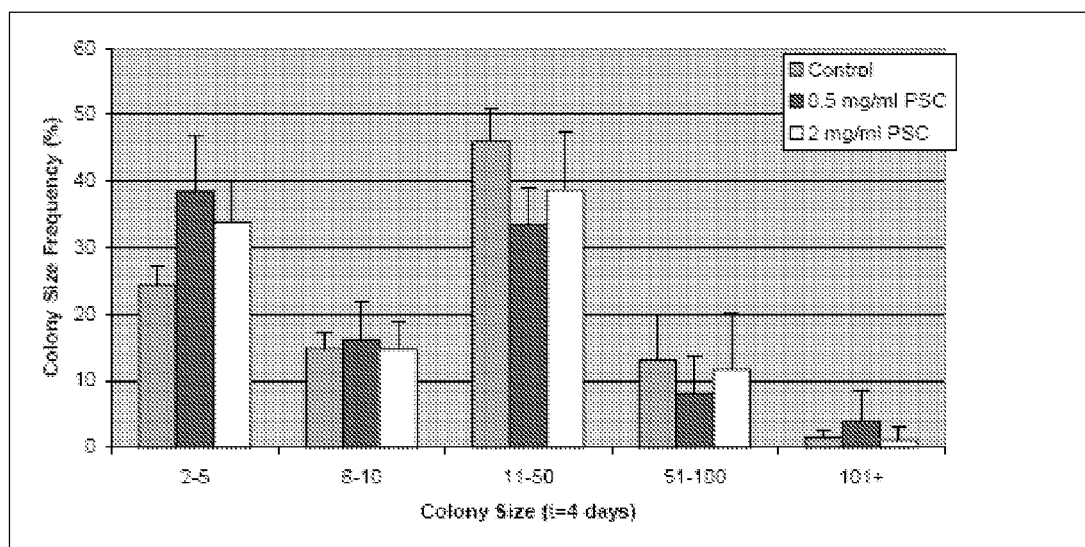
FIG. 9 shows a histogram of the colony size formed (t=4 days) by an EPC population before being seeded within 3D ECMs (Ctrl) and after being seeded at cell densities of $1\times10^5$ cells/ml within 3D ECMs polymerized at 0.5 mg/ml and 2.0 mg/ml PSC. Note the shift in the colony forming potential for the cells seeded under the different conditions. These data include colonies that contained at least 2 cells. (within each group represented on the abscissa; the left bar=control, middle bar=0.5 mg/ml PSC, right bar=2 mg/ml PSC).
Figure 10:
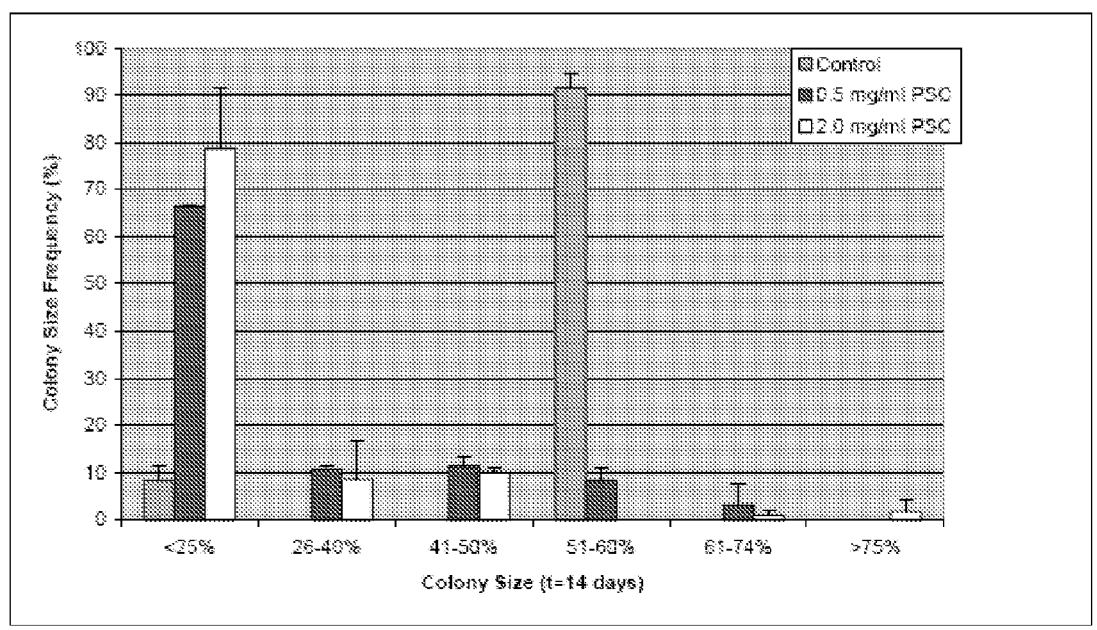
FIG. 10 shows a histogram of the colony size formed (t=14 days) by an EPC population before being seeded within 3D ECMs (Ctrl) and after being seeded at cell densities of $1\times10^5$ cells/ml within 3D ECMs polymerized at 0.5 mg/ml and 2.0 mg/ml PSC. Note the shift in the colony forming potential for the cells seeded under the different conditions. These data include single cell events. Note that EPCs grown within PSC show increased colony forming potential. (within each group represented on the abscissa; the left bar=control, middle bar=0.5 mg/ml PSC, right bar=2 mg/ml PSC).

Endothelial progenitor cells (EPCs; passage 9) were seeded at cell densities of $1\times10^5$ cells/ml within 3D ECMs polymerized at 0.5 mg/ml (fibril density of 6% and storage modulus of 44.64±8.03 Pa) and 2.0 mg/ml (fibril density of 16% and a storage modulus of 694.05±53.09 Pa) pig skin type I collagen (PSC). After 6 days of culture, cells were harvested from the ECMs using a collagenase cocktail (see Example 7). The cells then were analyzed using a colony forming assay. The colony forming potential for the EPCs prior to seeding within the matrices also was determined and served as a Control. The percentage of dividing cells was at 99.1±0.5%, 95.3±4.8%, and 96.3±3.9% for Control, 0.5 mg/ml PSC, and 2 mg/ml PSC groups, respectively. The colony size formed by an EPC population before being seeded within 3D ECMs (Ctrl) and after being seeded at cell densities of $1\times10^5$ cells/ml within 3D ECMs polymerized 0.5 mg/ml and 2.0 mg/ml was measured at 4 days (FIG. 8) and 14 days, (FIG. 10). Note the shift in the colony forming potential for the cells seeded under the different conditions. These data include single cell events. Measurements of colonies containing at least 2 cells at 4 days are shown in FIG. 9.

Example 6

Endothelial Progenitor Cells (EPCS)

Figure 11:
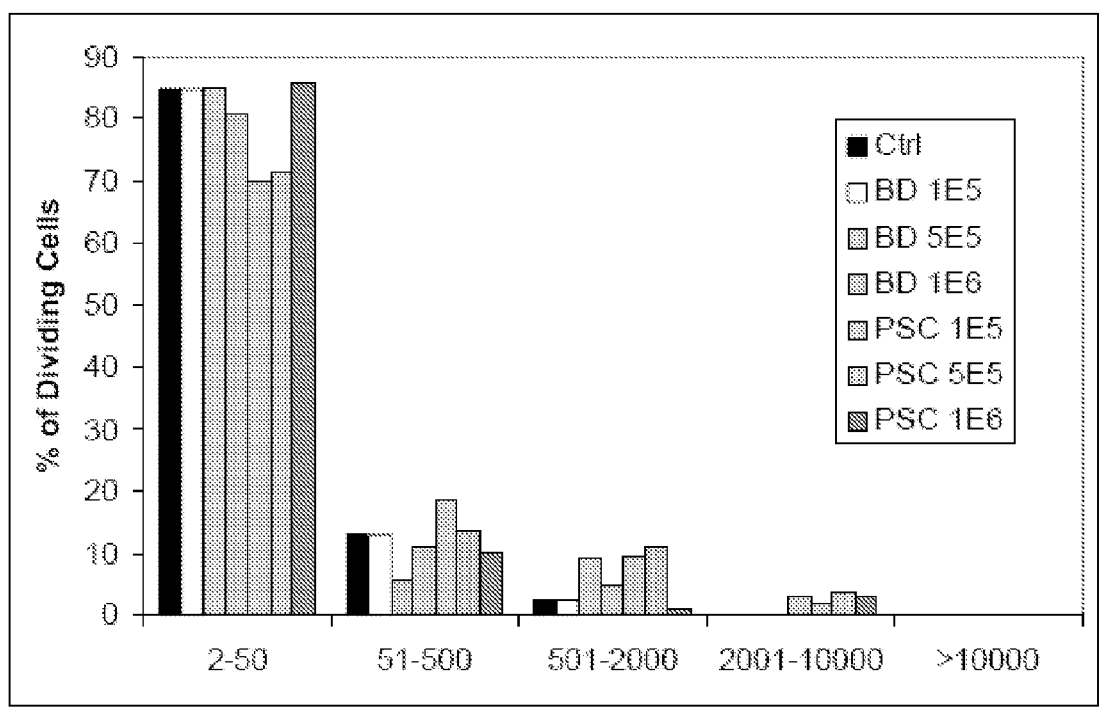
FIG. 11 shows a histogram of the colony size formed by an EPC population before being seeded within 3D ECMs (Ctrl) and after being seeded at cell densities of $1\times10^5$, $5\times10^5$, and $1\times10^6$ cells/ml within BD ECMs (1.5 mg/ml type I collagen+1 µg/ml fibronectin) or PSC ECMs (1.5 mg/ml pig skin type I collagen). Note the shift in the colony forming potential for the cells seeded under the different conditions. Note that EPCs grown within PSC show increased colony forming potential even at low seeding densities. (bars within each group (left to right) correspond to position in legend (top to bottom).
Figure 12:
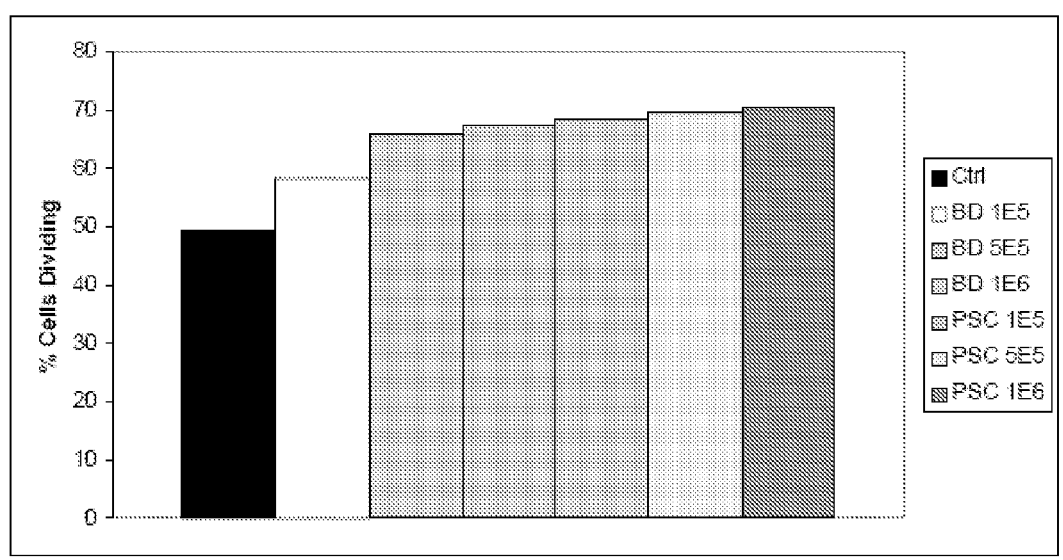
FIG. 12 shows the percentage of EPCs that underwent at least one cell division before being seeded within 3D ECMs (Ctrl) and after being seeded at cell densities of $1\times10^5$, $5\times10^5$, and $1\times10^6$ cells/ml within BD ECMs (1.5 mg/ml type I collagen+1 µg/ml fibronectin) or PSC ECMs (1.5 mg/ml pig skin type I collagen). Note the increase in the percentage of dividing cells that was obtained after EPCs were seeded within 3D ECMs. Upon comparison of EPCs grown within BD and PSC ECM formulations, it was observed that EPCs seeded at a given cell density showed the greatest proliferative potential within the PSC formulation. (bars within each group (left to right) correspond to position in legend (top to bottom).

Endothelial progenitor cells (EPCs) were seeded at cell densities of $1\times10^5$, $5\times10^5$, and $1\times10^6$ cells/ml within 3D ECMs prepared with either pig skin type I collagen (1.5 mg/ml) or type I collagen (1.5 mg/ml; BD Biosciences)+fibronectin (1 µg/ml) and maintained for 7 days. PSC and BD were used as designators for the pig skin collagen and commercial collagen+fibronectin formulations, respectively. After 7 days of culture, cells were harvested from the ECMs using an enzyme cocktail (see Example 7). The cells were then analyzed using a colony forming assay. The colony forming potential for the EPCs prior to seeding within the matrices also was determined and served as a Control (Ctrl). A shift in the colony forming potential was found for the cells seeded under different conditions. EPCs grown within PSC showed increased colony forming potential even at low seeding densities (FIG. 11). An increase in the percentage of dividing cells was obtained after EPCs were seeded within 3D ECMs (FIG. 12). Upon comparison of EPCs grown within BD and PSC ECM formulations, it was observed that EPCs seeded at a given cell density showed the greatest proliferative potential within the PSC formulation.

Example 7

Protocol for Removing Cells from Constructs with Collagenase

This protocol was developed and optimized for the effective recovery of single cells from 3D ECM constructs while maintaining maximum viability. The collagenase is from Worthington, Type IV, and is used at a 500 U/ml concentration in the EPC extraction media. The dispase (Neutral protease) is from Worthington, and is used in a range from 1-2.4 U/ml, preferably 2.4 U/ml, in the extraction media with the collagenase. The Extraction Media is the EPC media from Lonza (EGM-2, CC3162, including the single-quots and extra Hyclone serum which makes it 12% serum) with additional serum from Hyclone to make it 50% serum. Additional ingredients include Gibco TripLE trypsin, the regular EPC media with 12% serum, and Trypan Blue. Large orifice tips and pipettes are to be used when pipetting the cells. The following steps are then performed:

1. Make the Extraction Media (50% serum media), warm to 37° C. Calculate the amount of collagenase/dispase that will be needed (usually 1 ml per construct from a 24 well plate plus extra for loss during filtering). Weigh the correct amount of collagenase and dispase into a single tube and add the correct amount of Extraction Media. Sterile filter with a 0.2 µm syringe filter. Use immediately.

2. Into a 15 ml tube add 5 ml of the sterile collagenase/dispase solution.

3. With sterile forceps place 5 constructs from a 24 well plate into the tube.

4. Shake at 120 rpm, 37° C. for 20 minutes. Keep the tube at a 45° angle to increase the surface area. Flick the tube frequently.

5. Add an equal volume of Extraction Media. Pipet up and down gently.

6. Centrifuge at 1000 rpm for 5 minutes at room temperature.

7. Remove the supernatant and rack the tube with the remaining pellet.

8. Add 5 mL of regular EPC media, pipet up and down gently and centrifuge as in number 6.

9. Remove the supernatant and rack the tube with the remaining pellet.

10. Add 100 µl Gibco TrypLE and pipet up and down gently.

11. Shake at 120 rpm, 37° C. for 15 minutes. Flick the tube frequently.

12. Add 100 µl regular EPC media to stop the trypsin and pipet to mix.

13. Take 15 µl of the sample and add to 15 µl Trypan blue.

14. Do a cell count.

Example 8

Endothelial Colony Forming Cells (ECFCS)

Figure 13:
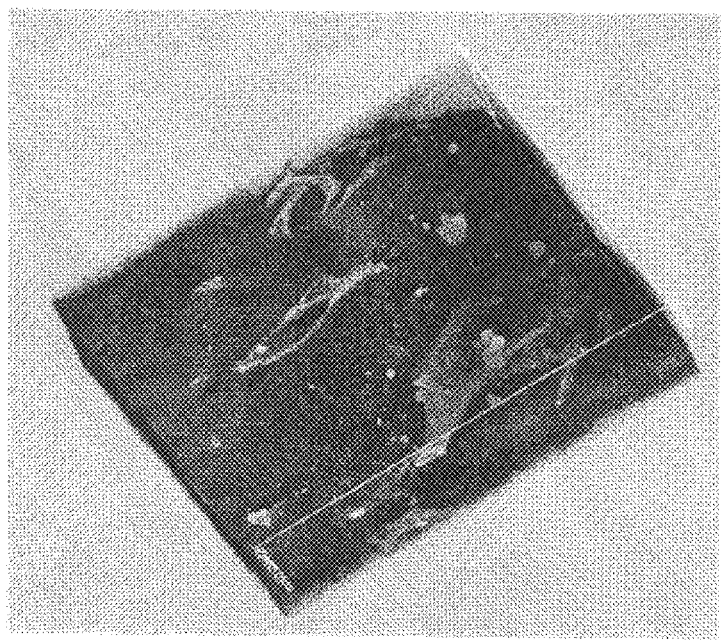
FIG. 13 shows an example of a microvessel network formed by endothelial colony-forming cells (ECFCs) seeded within engineered ECM prepared from pig skin collagen. ECFCs (bright white) were labeled with FITC conjugated UEA-1 lectin and collagen fibril microstructure was simultaneously visualized using 488 nm reflected light. Panel A illustrates both cellular and collagen fibril components of the construct. Panel B illustrates only cellular component.
Figure 13:
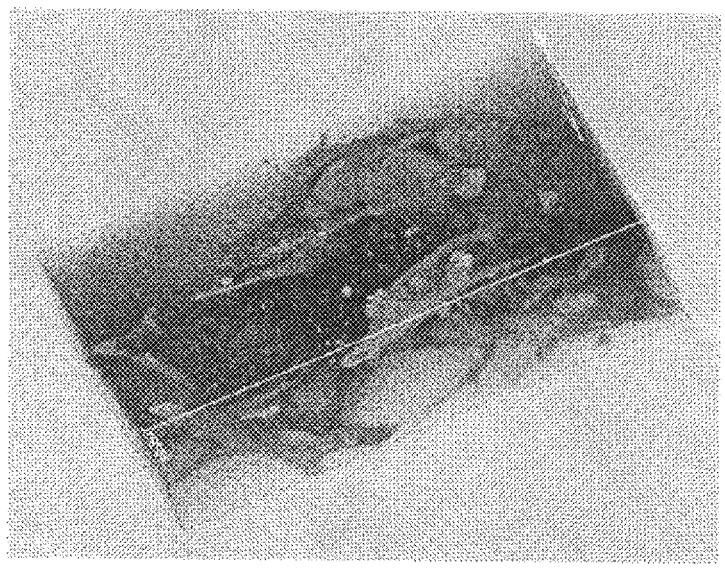
Figure 14:
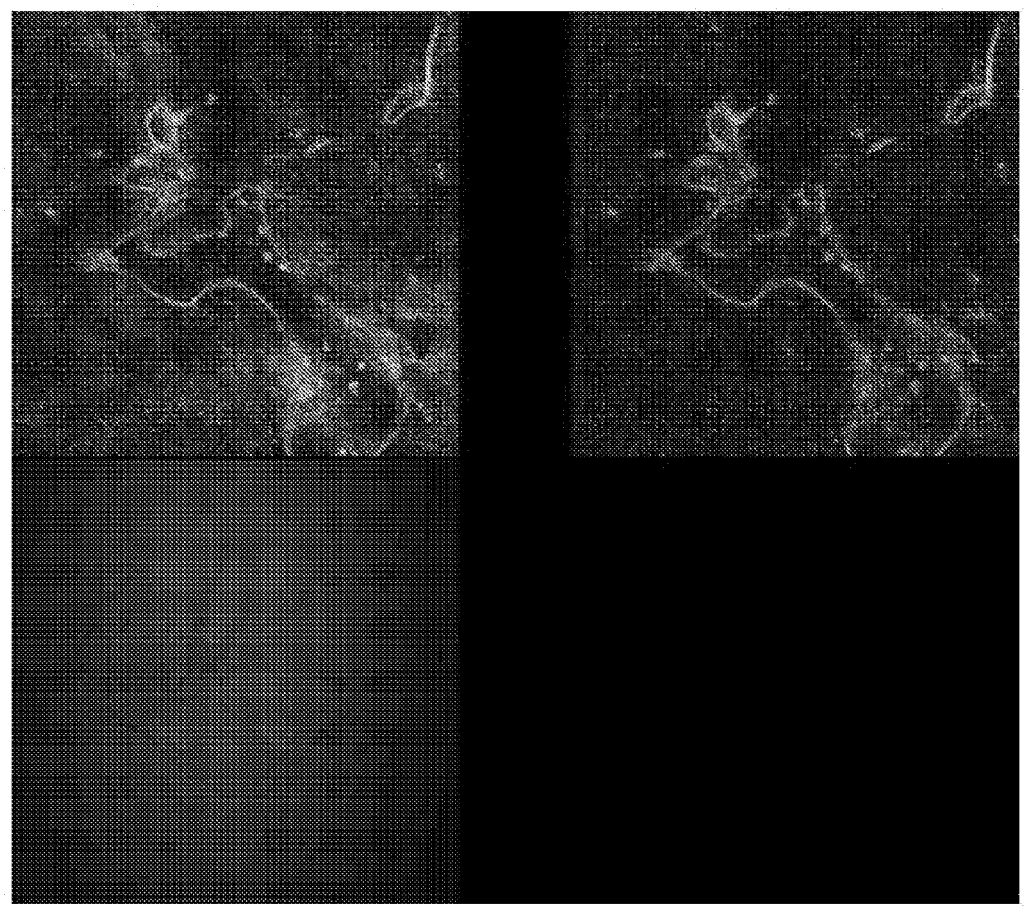
FIG. 14 shows ECFCs having formed endothelial-lined microvessels containing round, viable cells.

Endothelial colony forming cells (ECFCs) were seeded within engineered extracellular matrices prepared from pig skin collagen. ECFCs (bright white) were labeled with FITC conjugated UEA-1 lectin and collagen fibril microstructure was simultaneously visualized using 488 nm reflected light (FIG. 13). ECFCs formed endothelial-lined microvessels, some of which contained round, viable cells (FIG. 14).

Example 9

Figure 15:
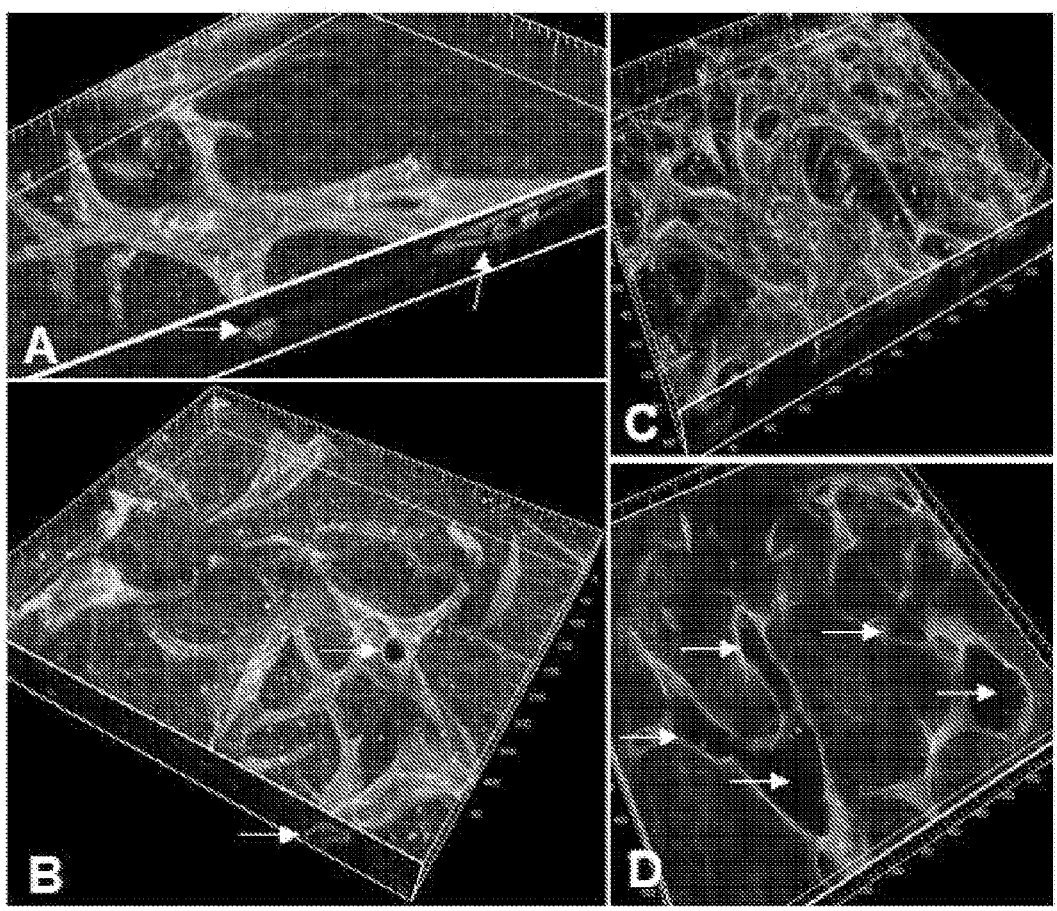
FIG. 15 shows 3D images demonstrating the differences in the vascular network development by ECFCs ($1\times10^5$ cells/ml) after 8 days within engineered ECMs prepared with pig skin collagen concentration, fibril volume fraction, and stiffness (G') of (Panel A) 2 mg/ml, 38%, and 767 Pa and (Panel B) 0.5 mg/ml, 9%, and 48 Pa. Panels C and D represent an extensive vascular network produced by ECFCs after 14 days of culture within an engineered ECM. Panel C shows the network of ECFCs and Panel D provides a volume slice clearly demonstrating the lumens present in the vascular network. ECFCs (bright white) were labeled with FITC conjugated UEA-1 lectin and collagen fibril microstructure was simultaneously visualized using 488 nm reflected light (arrows denote visible lumens). Major tick mark on all images equals 50 µm.

Type I Collagen 3D ECM Microenvironment Alters ECFC Vascular Network Formation In Vitro Endothelial colony forming cells (ECFCs) were isolated as previously described and suspended in collagen solutions prior to polymerization to ensure a uniform distribution throughout the type I collagen 3D ECM. To investigate the role of cell-cell interactions in ECM guidance of vascular network formation ECFCs were seeded at a density of about $1 \times 10^5$ to about $10^6$ cells/mL within engineered extracellular matrices and cultured for 8 or 14 days (FIG. 15).

Three dimensional images were taken that illustrate the differences in vascular network development by ECFCs prepared with pig skin collagen concentration, fibril volume fraction, and stiffness (G') of 2 mg/ml, 38%, and 767 Pa (FIG. 15, panel A) compared to 0.5 mg/ml, 9%, and 48 Pa (FIG. 15, panel B) after 8 days. FIG. 15, panels C and D represent an extensive vascular network produced by ECFCs after 14 days of culture within an engineered ECM. Panel C shows the network of ECFCs and Panel D provides a volume slice clearly demonstrating the lumens present in the vascular network. Fluorescence and reflection confocal microscopy were used to visualize the ECFC derived vascular structures and the surrounding collagen ECM respectively (FIG. 15). ECFCs (bright white) were labeled with FITC conjugated UEA-1 lectin and collagen fibril microstructure was simultaneously visualized using 488 nm reflected light (arrows denote visible lumens). The major tick mark on all images equals 50 µm.

These studies show a qualitative difference in structure formation and regression in the four ECM environments tested. Even in the absence of phorbol esters the ECMs were able to direct ECFC vascular structure formation. Vascular networks were largest and most complex around 72 hours and then these networks started to regress. Less vascular structure regression occurs in the pig skin collagen ECMs.

Example 10

Mechanical Properties of Type I Collagen ECMS

Figure 16:
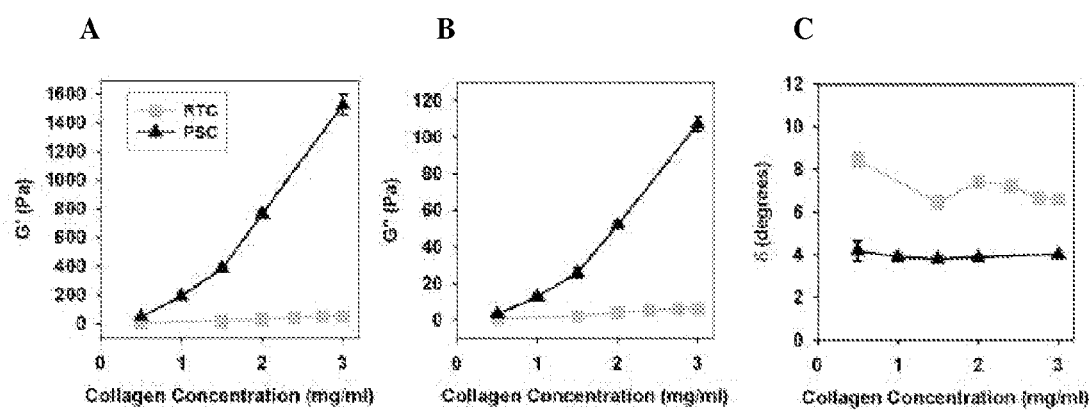
FIG. 16 shows the shear storage modulus, or stiffness, over a range of collagen concentrations for pig skin compared to rat tail collagen (Panel A). The pig skin collagen demonstrated a broader range for shear storage modulus than the rat tail collagen over the range of collagen concentrations measured. Panel B shows the shear storage modulus over the same range of collagen concentrations. Again, the pig skin collagen demonstrated a broader range of shear storage modulus. Panel C depicts delta, which is the phase shift of the strain and stress waves over the range of collagen concentrations. The rat tail collagen was found to have a higher delta, and thus a more viscous response.

An experiment was performed to study the microstructural-mechanical properties of two sources of collagen. An ECM from pig skin collagen was compared to an ECM from commercially available rat tail collagen (Becton-Dickinson) over a range of collagen concentrations, from about 0.5 mg/ml to about 3.0 mg/ml. Engineered 3D ECMs from rat tail and pig skin collagen showed distinct relationships between fibril microstructure and mechanical properties. FIG. 16, Panel A, shows the shear storage modulus, or stiffness, over a range of collagen concentrations for pig skin compared to rat tail collagen. The pig skin collagen demonstrated a broader range for shear storage modulus than the rat tail collagen over the range of collagen concentrations measured. FIG. 16, Panel B, shows the shear storage modulus over the same range of collagen concentrations. Again, the pig skin collagen demonstrated a broader range of shear storage modulus. FIG. 16, Panel C, depicts delta, which is the phase shift of the strain and stress waves over the range of collagen concentrations. The rat tail collagen was found to have a higher delta, and thus a more viscous response.

Figure 18:
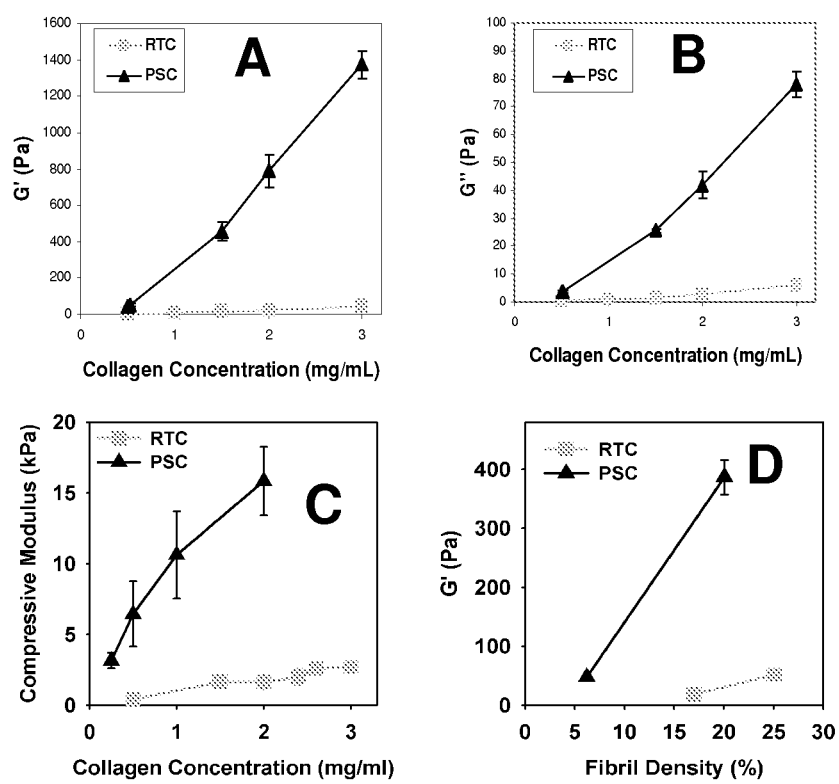
FIG. 18 shows the mechanical properties of the 3D ECMs from type I pig skin collagen (PSC) and rat tail collagen (RTC): Panel A shows shear storage modulus (G') of RTC and PSC ECMs versus collagen concentration; Panel B shows shear loss modulus (G") of RTC and PSC ECMs versus collagen concentration; Panel C shows compressive modulus of RTC and PSC ECMs versus collagen concentration; and Panel D shows shear storage modulus (G') versus fibril density for RTC and PSC ECMs. Values shown are the mean±standard deviation.

A Sirius red assay was used to verify the collagen concentration of both sources. Viscoelastic properties were determined for each collagen source using a TA Instruments AR-2000 rheometer adapted with a 40-mm plate geometry and a humidity trap. All samples were tested under oscillatory shear and at least 4 repetitions of each sample were completed. Each sample was allowed to self-assemble (polymerize) for 1 hour at 37° C. prior to strain sweep and unconfined compression analyses. A strain sweep was conducted in the linear viscoelastic range over a strain range of $1 \times 10^{-4}$ to $1 \times 10^{-2}$ and storage modulus (G') (stiffness) and the loss modulus (G") calculated. Each sample was then tested in unconfined compression and the compressive stiffness determined (FIG. 18). Confocal reflection microscopy was used to visualize the 3D fibril microstructure and the fibril volume fraction (fibril density) was determined as previously described [Voytik-Harbin, *J. Biomech. Eng.*, 124 (2): 214-22 (2002); incorporated herein by reference] (FIG. 18). The mechanical properties of the 3D ECMs from type I pig skin collagen (PSC) and rat tail collagen (RTC) are shown in FIG. 18, Panel A, as shear storage modulus (G') of RTC and PSC ECMs versus collagen concentration; FIG. 18, Panel B, as shear loss modulus (G") of RTC and PSC ECMs versus collagen concentration; FIG. 18, Panel C) compressive modulus of RTC and PSC ECMs versus collagen concentration; and FIG. 18, Panel D, as shear storage modulus (G') versus fibril density for RTC and PSC ECMs.

The relationship between stiffness (G') and fibril density is different for pig skin and rat tail collagen ECMs (FIG. 18, Panel D). As a result the stiffness (G') or fibril density for ECMs from the two different collagen sources can be matched but stiffness (G') and fibril density can not be matched simultaneously. However, using two collagen sources and 4 ECM microenvironments allowed the effects of the two parameters, stiffness (G') and fibril density, on the ability of the ECM to influence ECFC vascular structure formation to be determined.

Example 11

Characterization of Engineered ECM Microstructural-Mechanical Properties

Figure 17:
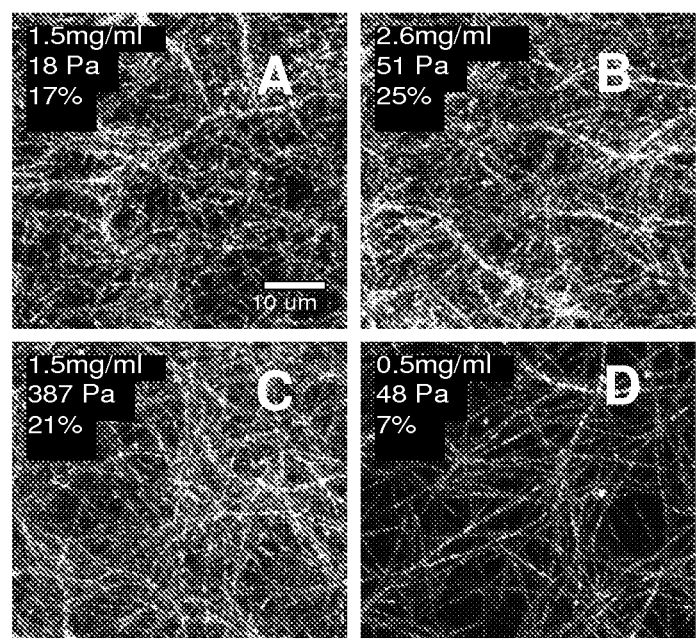
FIG. 17 shows the representative 2D projections of confocal reflection image stacks comparing the fibril microstructure for engineered ECMs prepared using commercial (Panels A and B) and pig skin (Panels C and D) collagen sources. Self-assembly conditions of both collagen sources were adjusted to yield engineered ECMs with the same fibril volume fraction (Panels A and C) or storage modulus (G', stiffness; Panels B and D). Initial collagen concentration, G', and fibril volume fraction data are provided.

Different ECM microenvironments were tested in these experiments and rat tail and pig skin collagen were found to produce ECMs with distinct mechanical properties. Representative 2D projections of confocal reflection image stacks comparing the fibril microstructure for engineered ECMs prepared using commercial (Panels A and B) and pig skin (Panels C and D) collagen sources are shown in FIG. 17.

Self-assembly conditions of both collagen sources were adjusted to yield engineered ECMs with the same fibril volume fraction (Panels A and C) or storage modulus (G', stiffness; Panels B and D). The rat tail collagen construct had a stiffness of 18 Pa and the pig skin collagen system had a stiffness of 387 Pa. FIG. 17 (Panels B and D) show a new set of rat tail and pig skin constructs designed to be matched in stiffness. Initial collagen concentration, G', and fibril volume fraction data are provided. FIG. 18, Panel D, shows the relationship between shear storage modulus and fibril density. This relationship was distinct in the two collagen sources, revealing that either collagen concentration or fibril density could be matched, but not both simultaneously.

From these studies, it is shown that for a given collagen concentration, ECMs from the pig skin collagen have a greater fibril density and stiffness (G'). Further, over the range of collagen concentrations investigated pig skin collagen yielded ECMs with a broader range of fibril microstructure and mechanical properties. From these mechanical studies four ECMs, two from each collagen source, that have either the same fibril density or stiffness (G') were selected to investigate the effects of ECM mechanical properties on ECFC vascular network formation (FIG. 17).

Example 12

Vascular Network Formation

Figure 19:
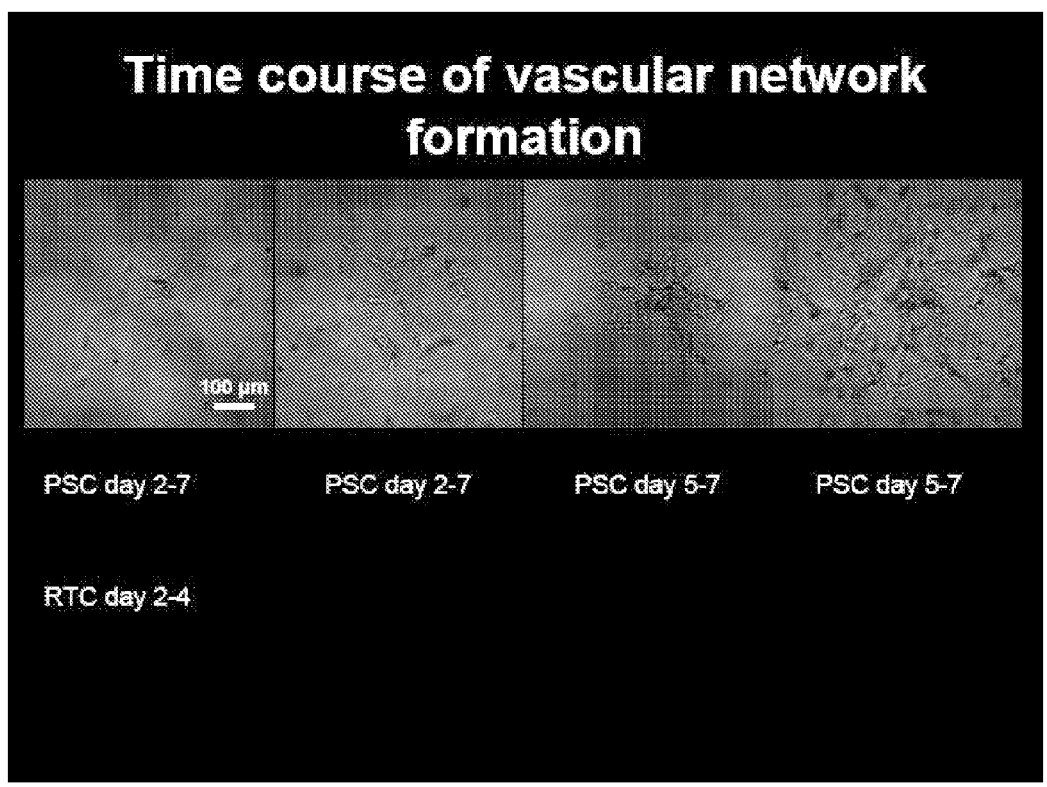
FIG. 19 shows the time course of vascular network formation.

Vascular network formation in culture was examined over time (FIG. 19). The first panel shows the smallest and least complex structures which typically appear at 2 days of culture. The structures persist in the pig skin collagen system but regress in the rat tail collagen system around day 5. The next panel depicts a step up in vascular structural complexity that also appears at around day 2 in the pig collagen system. These structures are not seen in the rat tail collagen system. The third and fourth panels show the two most complex vascular structures which appear at around day 5 in culture. Again such complex structures are only seen in the pig skin collagen system.

Example 13

Figure 20:
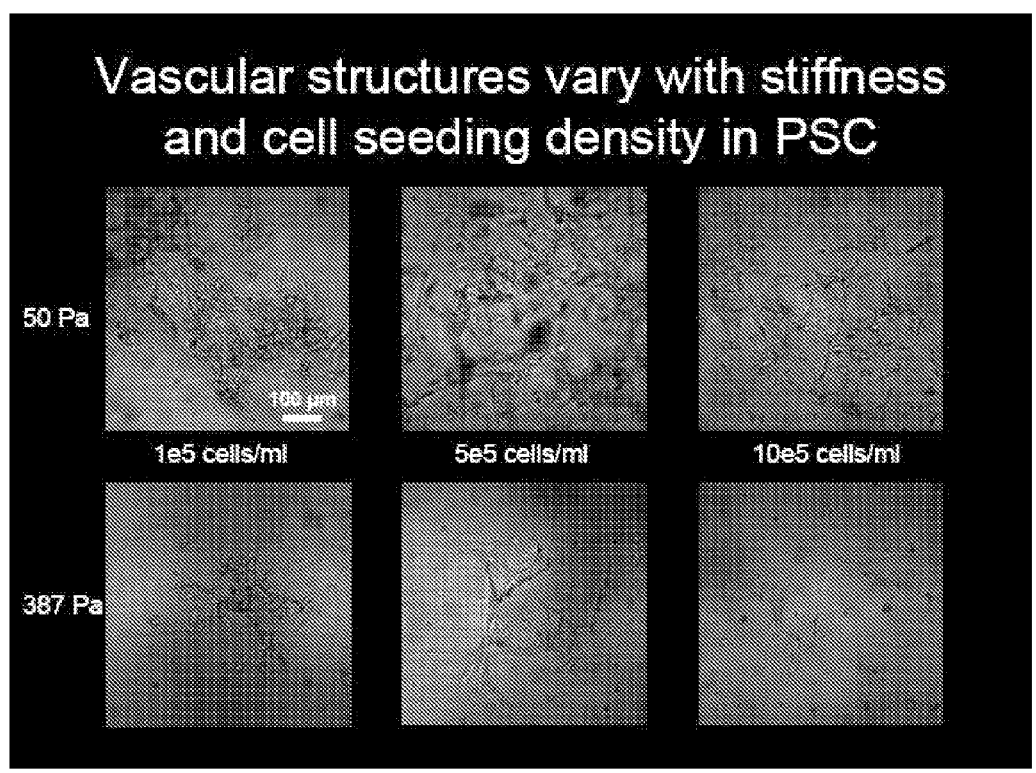
FIG. 20 shows the vascular structure complexity over varying stiffness and cell seeding density in the pig skin collagen construct.

Type I Collagen 3D ECM Microenvironment Alters ECFC Vascular Network Formation In Vitro Vascular structure complexity was found to vary with stiffness and cell seeding density in the pig skin collagen system (FIG. 20). The top row depicts representative structures in the 50 Pa, or low stiffness, pig collagen constructs. The first column shows a seeding density of $1 \times 10^5$ cells/ml. The second column depicts a seeding density of $5 \times 10^5$ cells/ml. The structures are larger and more complex at this seeding density. The third column is representative of $1 \times 10^6$ cells/ml, wherein the structures seen were typically smaller and less complex than at the seeding density of $5 \times 10^5$ cells/ml.

Figure 21:
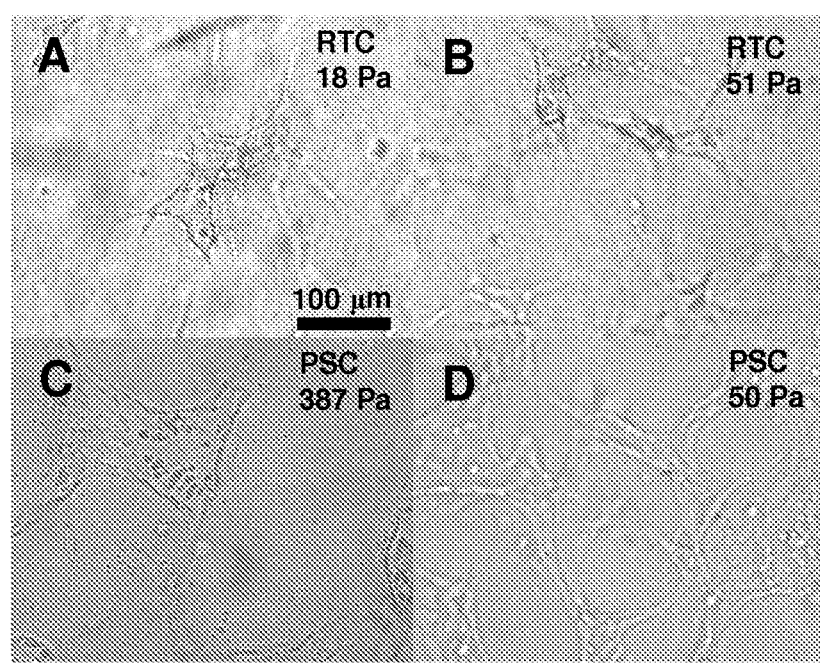
FIG. 21 show brightfield images of ECMs from rat tail collagen (RTC) (Panels A and B) and pig skin collagen (PSC) (Panels C and D). Stiffnesses are shown in Pascals (Pa).

Difference in stiffness (G') and fibril density affected size and complexity of ECFC vascular structures (FIG. 21). Vascular Structures were seen in all four ECMs during the seven day culture period. The pig skin collagen ECM with 48 Pa matrix stiffness (G') and 7% fibril density qualitatively had the largest and most complex vascular structures. This ECM had the lowest fibril density of the four ECMs tested and had an intermediate stiffness, indicating that both parameters are important in directing ECFC behavior. Brightfield images showed that ECMs from rat tail collagen (RTC) (Panels A and B) and pig skin collagen (PSC) (Panels C and D) were able to support ECFC vascular structure formation to varying degrees. ECMs depicted in Panels A and C have the same fibril density, while ECMs depicted in Panels B and D have the same stiffness (G'), shown in Pascals (Pa).

An increase in ECFC seeding density resulted in larger and more complex vascular structures in the rat tail collagen ECMs. In the pig skin collagen ECMs vascular structures seen with both seeding densities were of similar size and complexity as those seen in the rat tail collagen ECMs at a seeding density of $10^6$ cells/mL. One interpretation of these initial results is that the microstructure of the pig skin ECMs are better able to transmit ECFC generated mechanical signals that aid in the formation of multicellular structures prior to the cell-cell contacts being established.

Figure 22:
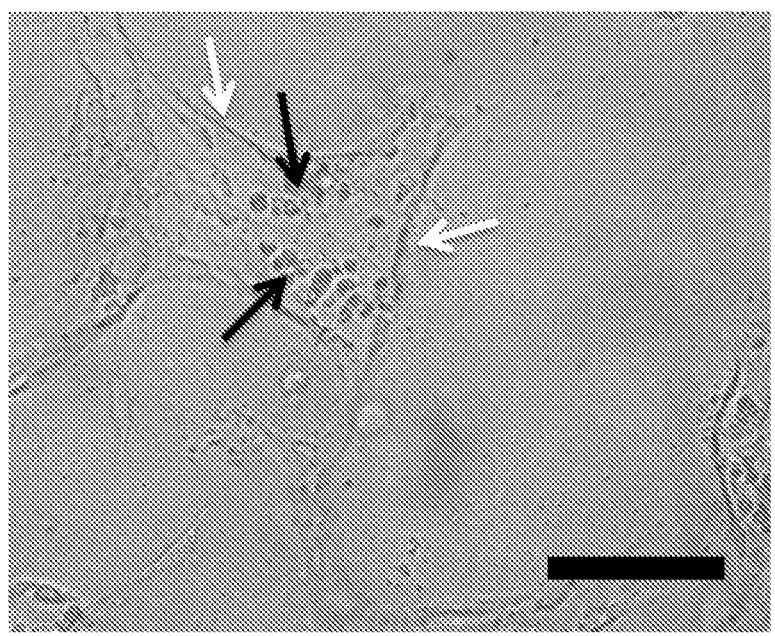
FIG. 22 shows a brightfield image of a vessel network formed by ECFCs cultured within a 3D collagen matrix. Distinct cellular phenotypes are noted as rounded cells (black arrows) found within the lumen of an endothelial lined vessel network (white arrows). Scale bar=100 µm.

ECFCs seeded within 3D collagen matrices undergo a morphogenesis process including vacuolization, cell proliferation, and a balance between cell-cell and cell-matrix interactions to form lumen-containing vessels. Under specific conditions, distinct populations of rounded cells are identifiable within the lumens of vessels, reminiscent of blood island formation as occurs in vasculogenesis during development (FIG. 22).

Example 14

Pig Skin and Rat Tail Type I Collagen ECMS Direct ECFC Blood Vessel Formation In Vivo ECFCs were suspended in either pig skin or rat tail collagen solution at $2 \times 10^6$ cells/mL and 1 mL of the solution was added to a 12 well tissue culture plate. The ECM polymerized for 20 minutes at 37° C. and then 2 mL of warm EGM-2 (Lonza, Basel, Switzerland) media was added. The ECFCs in ECMs were cultured overnight. The ECMs were bisected and then implanted subcutaneously into the flank of a mouse as previously described. NOD/SCID/$\gamma_c^{null}$ mice (T-, B-, & NK cell deficient, impaired complement) were chosen as the animal model to alleviate xenogenic barriers associated with implantation of human cells. After 14 days the mice were euthanized and the collagen ECMs were harvested, fixed in a formalin free fixative (BD Pharmingen, San Diego, Calif.), and embedded in paraffin. Sections 6 µm thick were cut and either stained with Hematoxylin and Eosin (H&E) or with antibodies to either mouse or human CD31 as previously described. A monoclonal mouse anti-human CD31 antibody (clone JC/70A, AbCam, Cambridge, Mass.) and an anti-mouse CD 31 antibody (clone mec 13.3, BD Pharmingen, San Diego, Calif.) were used to differentiate between vessels formed from human ECFCs and host vessels that may have invaded the ECM (FIG. 24).

Figure 24:
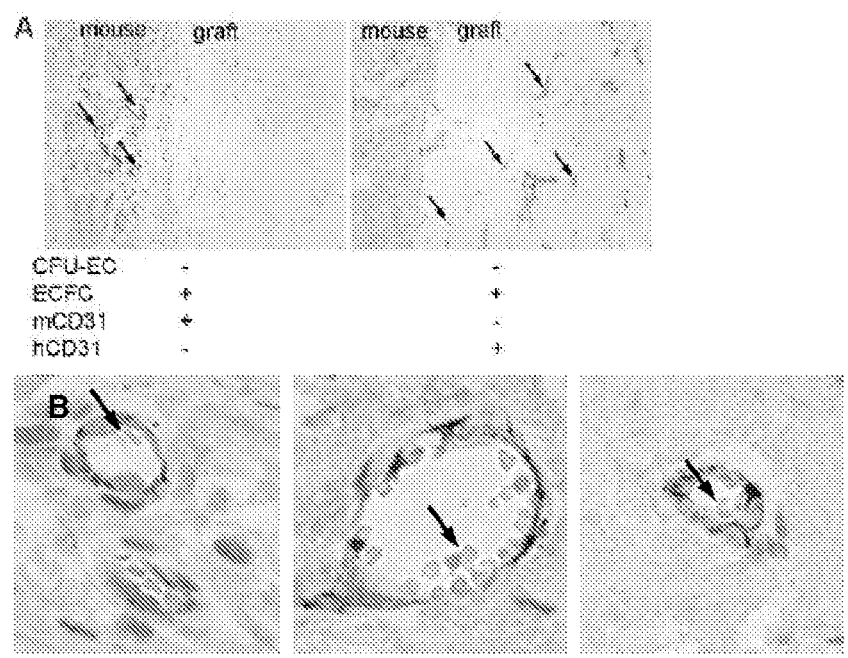
FIG. 24 shows ECM direct ECFC vessel formation in vivo. Panel A shows a photomicrograph (original magnification, ×20) of cellularized ECMs and surrounding mouse tissue. The two panels show consecutive sections of the same ECM stained with anti-mouse CD31 (mCD31) and anti-human CD31 (hCD31) to identify either mouse or human vessels respectively. Panel B shows a photomicrograph (original magnification, ×100) of ECFC vessels stained with hCD31. ECFC vessels and capillaries in the ECM are perfused with mouse red blood cells (arrows).

FIG. 24, Panel A shows a photomicrograph (original magnification, ×20) of cellularized ECMs and surrounding mouse tissue. The two panels show consecutive sections of the same ECM stained with anti-mouse CD31 (mCD31) and anti-human CD31 (hCD31) to identify either mouse or human vessels respectively. mCD31 does not cross-react with human ECFCs within the ECM and hCD31 does not cross-react with mouse ECs in vessels in the host tissue. FIG. 24, Panel B shows a photomicrograph (original magnification, ×100) of ECFC vessels stained with hCD31. ECFC vessels and capillaries in the ECM are perfused with mouse red blood cells (arrows) indicating anastomoses with mouse blood vessels.

A collagen-fibronectin ECM, previously shown to facilitate ECFC vessel formation, was used as a positive control. The mechanical properties of the collagen-fibronectin ECM were tested and the matrix stiffness (G') and fibril density were determined. Both the stiffness and fibril density were not significantly different then the 18 Pa rat tail collagen ECM (data not shown). These studies demonstrate that human umbilical cord blood derived ECFCs form blood vessels de novo in ECMs of both pig skin and rat tail collagen with matched fibril density (data not shown). Qualitative differences in the number of human vessels formed and the size of the vessels formed in the pig skin and rat tail collagen ECMs were seen.

Figure 25:
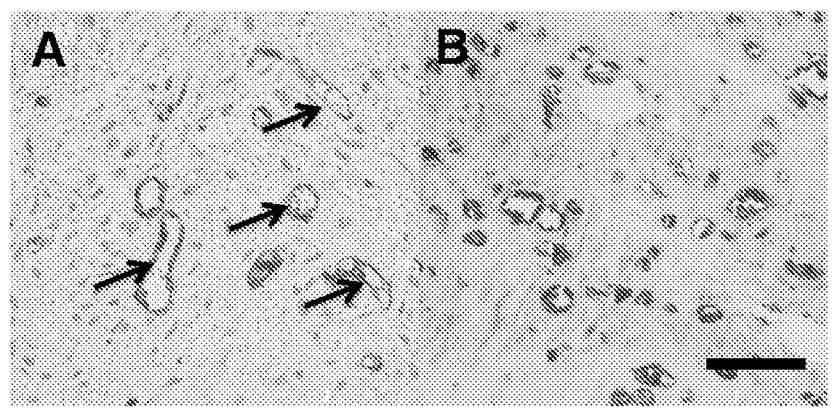
FIG. 25 shows histological cross-sections showing matrix-dependent ECFC response 2 weeks following subcutaneous implantation within NOD/SCID mice. ECFCs were implanted within collagen matrices that varied in fibril density and stiffness: Panel A=12% and 30 Pa (0.5 mg/ml) and Panel B=21% and 650 Pa (2.5 mg/ml). Functional vessels are indicated by arrows. Scale bar=50 µm.

The ability of ECFCs to form vessels with anastomoses to host vessels in vivo is dependent upon the fibril microstructure-mechanical properties of the delivery collagen matrix (FIG. 25). Histological cross-sections showing matrix-dependent ECFC response 2 weeks following subcutaneous implantation within NOD/SCID mice are shown. ECFCs were implanted within collagen matrices that varied in fibril density and stiffness, (FIG. 25, Panel A) 12% and 30 Pa (0.5 mg/ml); and (FIG. 25, Panel B) 21% and 650 Pa (2.5 mg/ml). Sections were stained for anti-human CD31 and counterstained with H&E. Numerous functional vessels (arrows) were noted within the 50 Pa matrix. In contrast, vessels formed within the 650 Pa matrix failed to anastomose with host vessels.

Example 15

USSCS Aid in ECFC Blood Vessel Formation in a Type I Collagen 3D ECM In Vivo

ECFCs and USSCs were suspended in fibronectin-rat tail collagen solution at a ratio of 4:1 while maintaining the total cell seeding density at $2 \times 10^6$ cells/mL. ECFCs and USSCs were also suspended individually in fibronectin-rat tail collagen solution at $2 \times 10^6$ cells/mL. As before, 1 mL of the solution was added to a 12 well tissue culture plate. The ECM was allowed to polymerize for 20 minutes at 37° C. and then 2 mL of warm EGM-2 media was added. The ECFCs in ECMs were cultured overnight. The ECMs were bisected and then implanted subcutaneously into the flank of a NOD/SCID/$\gamma_c^{null}$ mouse as previously described.

After 14 days, the mice were euthanized and the collagen ECMs were harvested, fixed in a formalin free fixative (BD Pharmingen, San Diego, Calif.), embedded in paraffin and 6 μm sections were cut. Sections were either stained with Hematoxylin and Eosin (H&E) or with antibodies to either mouse or human CD31 as previously described. ECFC and USSC co-culture in rat tail collagen-fibronectin ECMs formed 26.14±8.32 (mean±standard deviation) functional blood vessels, while ECFCs embedded alone formed 16.83±7.12 functional blood vessel showing USSC stabilization of ECFC derived vessels. USSC seeded alone in a rat tail type I collagen ECM significantly contracted the ECM but did not form any blood vessels (data not shown).

USSCs commit to different lineages within the ECM. ECMs implanted with both ECFCs and USSCs stain positive with Von Kossa, an indication of calcium deposition, and 1% Alcian blue in dye in glacial acetic acid, indicating chondrogenic differentiation (data not shown).

Example 16

Localized Delivery of ECFC in a Type I Collagen 3D ECM Impacts Wound Healing In Vivo Type I collagen 3D ECMs direct ECFC vessel formation and improve wound healing. A full thickness skin wound model was developed which utilized NOD/SCID/$\gamma_c^{null}$ mice. A 5 mm circular punch biopsy wand was used to remove a 5 mm area of full thickness skin. ECFCs were injected into the periphery of the wound in either EBM-2, a basal media, or in the collagen-fibronectin ECM. Each wound received four injections of 25 μL evenly spaced around the periphery using a 100 μL Hamilton syringe. EBM-2 or collagen-fibronectin without ECFCs was injected into the periphery of the wound as a negative control. Pictures of the wounds were taken daily for two weeks and the wound areas were calculated using Metamorph (Molecular Devices, Sunnyvale, Calif.). The change in wound area from initial wounding to the end of the study was calculated and then normalized by initial wound size. Results show localized delivery of ECFCs in rat tail collagen-fibronectin ECM reduce the wounds to 6.2±3.1% (mean±standard deviation) of original wound size compared to EBM-2 alone 19.6±17.5%, ECM alone 19.3±16.2%, and ECFCs in ECM 21.6±25% of original wound size (n=3) (data not shown).

What is claimed is:

1. A tissue graft composition, said composition comprising:
    an engineered, purified collagen-based matrix comprising collagen fibrils, wherein the matrix has a collagen fibril microstructure including fibril-fibril branching; and
    a network of lumenized, endothelial cell-lined vessels formed in vitro, said vessels capable of persisting for more than 7 days in vitro;
    wherein said collagen fibrils are polymerized from a pig skin collagen source comprising a mixture of type I collagen monomers and oligomers, wherein the concentration of collagen in the polymerization reaction is 0.3 mg/ml to 1 mg/ml, wherein the vessels are formed from endothelial progenitor cells, and wherein the matrix has a shear storage modulus of 40 Pa to 50 Pa and a fibril volume fraction of 5% to 10%; and
    wherein the tissue graft composition is produced by engineering the purified collagen-based matrix, and seeding the matrix at a density of $1 \times 10^5$ to $5 \times 10^5$ endothelial progenitor cells per milliliter to form one or more vessels within the matrix.

2. The tissue graft composition of claim 1, wherein said matrix has a loss modulus of from about 1 Pa to about 75 Pa.

3. The tissue graft composition of claim 1, wherein said matrix has a compression modulus of 2,500 Pa to about 18,000 Pa.

* * * * *